United States Patent
Klimasauskas et al.

(10) Patent No.: US 8,822,146 B2
(45) Date of Patent: *Sep. 2, 2014

(54) DERIVATIZATION OF BIOMOLECULES BY COVALENT COUPLING OF NON-COFACTOR COMPOUNDS USING METHYLTRANSFERASES

(75) Inventors: Saulius Klimasauskas, Vilnius (LT); Zita Liutkeviciute, Vilnius (LT); Edita Kriukiene, Vilnius (LT)

(73) Assignee: Vilnius University, Vilnius (LT)

( * ) Notice: Subject to any disclaimer, the term of this patent is extended or adjusted under 35 U.S.C. 154(b) by 83 days.

This patent is subject to a terminal disclaimer.

(21) Appl. No.: 13/262,340

(22) PCT Filed: Apr. 1, 2010

(86) PCT No.: PCT/EP2010/054436
§ 371 (c)(1),
(2), (4) Date: Dec. 19, 2011

(87) PCT Pub. No.: WO2010/115846
PCT Pub. Date: Oct. 14, 2010

(65) Prior Publication Data
US 2012/0094280 A1    Apr. 19, 2012

(30) Foreign Application Priority Data

Apr. 2, 2009  (LT) .................................... 2009 023
May 8, 2009  (LT) .................................... 2009 032

(51) Int. Cl.
*C12Q 1/68* (2006.01)
*C07H 21/04* (2006.01)
*C12P 19/34* (2006.01)

(52) U.S. Cl.
USPC .......... 435/6.1; 435/91.5; 435/193; 536/23.1; 536/28.5

(58) Field of Classification Search
None
See application file for complete search history.

(56) References Cited

U.S. PATENT DOCUMENTS 7,465,544 B2   12/2008  Rajski et al.

FOREIGN PATENT DOCUMENTS

| WO | WO 00/06587 | 2/2000 |
|---|---|---|
| WO | WO 2006/108678 | 10/2006 |
| WO | WO 2010/115847 | 10/2010 |

OTHER PUBLICATIONS

PCT, International Search Report, International Application No. PCT/EP2010/054436 (mailed Jul. 26, 2010, published Oct. 14, 2010).

Cheng, X., Structure and Function of DNA Methyltransferases, *Annual Review of Biophysics and Biomolecular Structure*, vol. 24, No. 1, pp. 293-318 (Jan. 1, 1995).
Alegria, A.H., Hydroxymethylation of Pyrimidine Mononucleotides with Formaldehyde, *Biochimica et Biophysica Acta*, No. 149, No. 2, pp. 317-324 (Dec. 19, 1967).
Flaks, J.G. et al., Virus-induced Acquisition of Metabolic Function. I. Enzymatic Formation of 5-Hydroxymethyldeoxycytidylate, *Journal Biological Chemistry*, vol. 234, No. 6, pp. 1501-1506 (Jun. 1, 1959).
Grafstrom, R.C. et al., Pathobiological effects of acetaldehyde in cultured human epithelial cells and fibroblasts, *Carcinogenesis*, vol. 15, No. 5, pp. 985-990 (1994).
Liukeviciute, Z. et al., Cytosine-5-methyltransferases add aldehydes to DNA, *Nature Chemical Biology*, vol. 5, No. 6, pp. 400-402 (May 10, 2009).
Bird, (2002), "DNA Methylation Patterns and Epigenetic Memory," Genes Dev. 16, 6-21.
Bong and Ghaderi, (2001), "Chemoselective Pd(0)-Catalyzed Peptide Coupling in Water," Org. Lett. 3, 2509-2511.
Cannon et al., (1988), "5-Hydroxymethylcytosine DNA Glycosylase Activity in Mammilian Tissue," Biochem. Biophys. Res. Commun. 151, 1173-1179.
Casalnuovo and Calabrese, (1990), Palladium-Catalyzed Alkylations in Aqueous Media, J. Am. Chem. Soc. 112, 4324-4330.
Dalhoff et al., (2006), "Direct Transfer of Extended Groups from Synthetic Cofactors by DNA Methyltransferase," Nat. Chem. Biol. 2, 31-32.
Dawson et al., (1994), "Synthesis of Proteins by Native Chemical Ligation," N-terminal cysteine residues of polypeptides, native chemical peptide ligation. Science 266, 776-779.
DeVasher et al., (2004), "Aqueous-Phase, Palladium-Catalyzed Cross-Coupling of Aryl Bromides under Mild Conditions, Using Water-Soluble, Sterically Demanding Alkylphosphines," J. Org. Chem. 69, 7919-7927.

(Continued)

*Primary Examiner* — Lisa J Hobbs
(74) *Attorney, Agent, or Firm* — Thompson Hine LLP

(57) ABSTRACT

The present invention relates to a use of non-cofactor compounds, represented by formulas (I) or (II) wherein R and Z are independently selected from H, D, $C_1$-$C_{12}$-alkyl, preferably $C_1$-$C_4$-alkyl, alkenyl, alkinyl, phenyl or -LX, wherein X represents a functional group or a reporter group attached via a linker group L, and QH is selected from —SH, —SeH, —NHNH$_2$ or —ONH$_2$, for a targeted modification or derivatization of a biomolecule by covalent coupling to the biomolecule in the presence of a directing methyltransferase. Further development of the method of targeted modification and derivatization are the method for targeted labeling a biomolecule and method for detecting unmethylated target sites in a biomolecule comprising modification of the biomolecule according to the present invention.

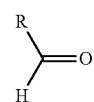

(I)

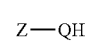

(II)

22 Claims, 6 Drawing Sheets

(56) References Cited

OTHER PUBLICATIONS

Dibowski and Schmidtchen, (1998), "Bioconjugation of Peptides by Palladium-Catalyzed C-C Cross-Coupling in Water," Angew. Chem. Int. Ed. 37, 476-478.
Goll, "Eurkaryotic Cystosine Methyltransferases," M.G. & Bestor, T.H. Annu. Rev. Biochem. 74, 481-514 (2005).
Graham et al., (2002), "Internal Labeling of Oligonucleotide Probes by Diels-Alder Cycloaddition," Tet. Lett. 43, 4785-4788.
Klimasauskas and Lukinavicius (2008), AdoMet-Dependent Methyltransferases, Chemistry of, Wiley Encyclopedia of Chemical Biology. DOI: 10.1002/9780470048672.wecb335, 1-10.
Klimasauskas and Weinhold, (2007), "A New Tool for Biotechnology: AdoMet-dependent methyltransferases," Trends Biotechnol. 25, 99-104.
Kutter and Wiberg, "Biological Effects of Substituting Cytosine for 5-Hydroxymethylcytosine in Deoxyribonucleic Acid of Bacteriophage T4," (1969) J. Virol. 4, 439-453.
LaFrancois et al. (1998), "Synthesis and Characterization of Isotopically Enriched Pyrimidine Deoxynucleoside Oxidation Damage Products," Chem. Res. Toxicol., 11, 75-83.
Lariviere and Morera (2002), "A Base-flipping Mechanism for the T4 Phage β-Glucosyltransferase and Identification of a Transition-state Analog," J. Mol. Biol. 324, 483-490.
Lariviere et al., (2005), "Structural Evidence of a Passive Base-flipping Mechanism for AGT, an Unusual GT-B Glycosyltransferase," J. Mol. Biol. 352, 139-150.
Lewis et al. (2002), "Click Chemistry In Situ: Acetylcholinesterase as a Reaction Vessel for the Selective Assembly of a Femtomolar Inhibitor from an Array of Building Blocks," Angew. Chem. Int. Ed. 41, 1053-1057.
Liu and Tam, (1994) "Peptide segment ligation strategy without use of protecting groups," Proc. Natl. Acad. Sci. USA 91, 6584-6588.
Lukinavicius et al., (2007), "Targeted Labeling of DNA by Methyltransferase-Directed Transfer of Activated Groups (mTAG)," J. Am. Chem. Soc. 129, 2758-2759.
Merkiene and Klimasauskas, "Probing a rate-limiting step by mutational perturbation of AdoMet binding in the HhaI methyltransferase," (2005) Nucleic Acids Res. 33, 307-315.
Pignot et al., (2000), "Efficient Synthesis of S-Adenosyl-L-Homocysteine Natural Product Analogues and Their Use to Elucidate the Structural Determinant for Cofactor Binding of the DNA Methyltransferase M-HhaI," Eur. J. Org. Chem. 549-555.
Pljevaljcic et al., (2004), "Sequence-Specific Methyltransferase-Induced Labeling of DNA (SMILing DNA)," ChemBioChem 5, 265-269.
Pljevaljcic et al., (2003), "Design of a New Fluorescent Cofactor for DNA Methyltransferases and Sequence-Specific Labeling of DNA," J. Am. Chem. Soc. 125, 3486-3492.
Pljevaljcic et al., (2004), "Sequence-Specific DNA Labeling Using Methyltransferases," Methods Mol. Biol. 283, 145-161.
Poletayev et al., (1976) Mol. Biol. (Mosk),10, 682-685 (English Abstract).
Rusmintratip and Sowers (2000), An unexpectedly high excision capacity for mispaired 5-hydroxymethylated in human cell extracts, PNAS 97, 14183-14187.
Saxon and Bertozzi, (2000), "Cell Surface Engineering by a Modified Staudinger Reaction," Science 287, 2007-2010.
Tardy-Planechaud et al., (1997), "Solid phase synthesis and restriction endonuclease cleavage of oligodeoxynucleotides containing 5-(hydroxymethylated)-cytosine," Nucleic Acids Res. 25, 553-558.
Zhang et al.: (2006), "Natural Product Diversification using a Non-natural Cofactor Analogue of S-Adenoysl-L-methionine," J. Am. Chem. Soc. vol. 128, pp. 2760-2761.
Dalhoff, C. (2005), Neue S-Adenosyl-L-methionin-Analoga mit Modifikationen im Methionin-Teil für Transalkylierungen mit DNA-Methyltransferasen Dokt. Diss, Aachener Beiträger zur Chemie, Bd. 63; ISBN 3-86130-767-7, pp. 1-174.
Garman A., Non-Radioactive Labeling: A Practical Introduction, Biological Techniques Series, Academic Press (1997), pp. 1-132.
Ignashov VG., Influence of Antibodies Against DNA on the Renaturation of DNA., Mol Biol (Mosk). Jul.-Aug. 1976;10(4): 682-685. (Abstract only).
House H.O. *Modern synthetic reactions*, $2^{nd}$ ed., W.A. Benjamin, NY, 1972 pp. 353-363.
Dalhoff, C. Novel S-adenosyl-L-methionine analogs with modifications in the methionine part for transalkylations with DNA-methyltransferases. Dissertation, RWTH Aachen University (2005), 14 pages (title and presentation pages (2 pages), Contents (7 pages), E2. Modifications to the activated side chain of AdoMet (5 pages noted as pp. 117-121)) (originally provided in a Jul. 16, 2012 Information Disclosure Statement but in German, title page, table of contents select portions now provided in English).

DERIVATIZATION OF BIOMOLECULES BY COVALENT COUPLING OF NON-COFACTOR COMPOUNDS USING METHYLTRANSFERASES

PRIORITY CLAIM

This application is a National Phase of PCT/EP2010/054436 filed Apr. 1, 2010, which claims priority to Lithuanian Patent Application No. LT2009023 filed Apr. 2, 2009 and Lithuanian Patent Application No. LT2009032 filed May 8, 2009.

FIELD OF THE INVENTION

The present invention relates to methyltransferase-directed covalent coupling of carbon electrophiles such as aldehydes to biomolecules and also to their subsequent methyltransferase-directed coupling with nucleophiles such as thiols, namely relates to methyltransferase-directed coupling to a biomolecule of any compound represented by formulas (I) or (II)

wherein R and Z are independently selected from H, D, $C_1$-$C_{12}$-alkyl, alkenyl, allkinyl, phenyl or -LX, wherein X represents a functional group or a reporter group, attached via a linker group L, and QH is selected from —SH, —SeH, —NHNH$_2$ or —ONH$_2$. This invention also covers a method for targeted modification, derivatization and labeling of a biomolecule as well as a method for detecting unmethylated target sites in a biomolecule and a kit for performing the methods mentioned, all grounded on the idea of covalent coupling of exogenous non-cofactor compounds, represented by formulas (I) or (II) above to the biomolecule in the presence of a directing methyltransferase.

The present invention is exemplified using DNA methyltransferases (MTases). However, it can also be used with RNA and protein methyltransferases as well as methyltransferases acting on other biomolecules.

In this description the term "methyltransferase" refers to enzymes that normally transferring the methyl from S-adenosyl-L-methionine (AdoMet) onto their substrate.

Preferably, the methyltransferase is an enzyme capable of methylating DNA, RNA or (poly)peptides. More preferably, the methyltransferase is a DNA cytosine-5 methyltransferase that uses a covalent activation mechanism for the transfer of the methyl groups on the C5 position of a target cytosine residue. More preferably, the methyltransferase is selected from M.Hhal, M.Sssl, M.Hpall, M.Alul or a derivative thereof. The term "M.Hhal" refers to the DNA methyltransferase deposited in the Swissprot database under accession number P05102.

The term "coupling" means chemical addition of a compound by making a stable covalent bond (such as a C—C bond, C—S bond, C—Se bond or C—N bond). The coupling reaction can be an addition of an entire electrophilic compound (I) to a target biomolecule or a (subsequent) condensation of a nucleophilic compound (II) whereby a hydroxyl group in the modified target biomolecule is replaced with an entire molecule of compound II.

The term "biomolecule" means DNA, RNA or (poly)peptide. The term "(poly)peptide" refers alternatively to peptide or to polypeptide. Preferably, the biomolecule is chromosomal or genomic DNA. Biomolecules may be entirely natural, i.e. unmodified, synthetic or modified and may exist as complexes. For example the term "nucleic acid molecule" comprises DNA and RNA molecules or RNA/DNA hydrids as well as modified DNA and RNA molecules. DNA may be for example cDNA or genomic DNA. RNA may be for example mRNA, hnRNA, tRNA, rRNA etc.

The term "derivatization" means modification of a biomolecule by covalent addition of chemical entities, such as carbon chains, chemically reactive groups or reporter groups into biomolecules, such as DNA without otherwise changing the target biomolecule.

BACKGROUND OF THE INVENTION

Besides the four major nucleosides (2'-deoxycytidine (dC), 2'-deoxyadenosine (dA), 2'-deoxyguanosine (dG) and 2'-deoxythymidine (dT)), DNA of most living organisms contains minor amounts of methylated nucleosides: 5-methyl-2'-deoxycytidine ($dC^{methyl}$), N4-methyl-2'-deoxycytidine and N6-methyl-2'-deoxyadenosine. These methylated species are formed by DNA methyltransferase enzymes (MTases) which catalyze the transfer of an activated methyl group from the cofactor S-adenosyl-L-methionine (AdoMet) to form the above methylated nucleotides within their DNA recognition sequences (Cheng, (1995) *Annu. Rev. Biophys. Biomol. Struct.* 24, 293-318). DNA methylation is an important biological mechanism that regulates gene expression in vertebrate animals including humans (Bird, (2002) *Genes Dev.* 16, 6-21), Goll, M. G. & Bestor, T. H. *Annu. Rev. Biochem.* 74, 481-514 (2005) and serves as a species self-code in bacteria. The AdoMet cofactor is universal for most methylation reactions in living organisms. This biologically and chemically active compound is comprised of a positively charged sulfonium center which joins three peripheral parts: the transferable methyl group, the adenosyl moiety and the homoserine moiety. The adenosyl and homoserine moieties typically serve as anchors which are required for discrete binding and correct orientation of the methyl group in a methyltransferase enzyme. The sulfonium center is thought to activate the methyl group for its transfer onto nucleophilic targets. Some methyltransferases also assist in activation of their target molecules by different mechanisms (Klimasauskas and Lukinavicius (2008) *Wiley Encyclopedia of Chemical Biology*. DOI: 10.1002/9780470048672.wecb335).

The ability of methyltransferases to catalyze sequence-specific, covalent modifications of biopolymers makes them potential tools for biotechnology. Recently, labeling strategies using three types of designer cofactors for DNA methyltransferases have been presented (Klimasauskas and Weinhold, (2007) *Trends Biotechnol.* 25, 99-104). One such strategy is based on replacing the methylgroup and the homoserine moiety of the natural cofactor S-adenosyl-L-methionine (AdoMet) by an aziridinyl moiety. These analogs confer methyltransferase-directed nucleophilic opening of the aziridine ring and coupling of the whole cofactor molecule to a target adenine or cytosine residue in DNA. Attachment of a fluorophore via a flexible linker to certain positions of the adenosyl moiety may not interfere with cofactor binding. These cofactors, such as 8-amino[1"-(N"-dansyl)-4"-aminobutyl]-5'-(1-aziridinyl)-5'-deoxyadenosine (Pljevaljcic et al., (2003) *J. Am. Chem. Soc.* 125, 3486-3492) or 8-amino

[1"-(N"-biotinyl)-4"-aminobutyl]-5'-(1-aziridinyl)-5'-deoxyadenosine (Pljevaljcic et al., (2004) *Methods Mol. Biol.* 283, 145-161) can be used for sequence-specific labeling of biomolecules (Pljevaljcic et al., (2004) *Chem Bio Chem* 5, 265-269). Aziridine derivatives are also disclosed (WO0003587, publ. 2000) which can be used as cofactor for S-adenosyl-L-methionine-dependent methyltransferases. Labeling is carried out by using AdoMet-dependent MTases, and the adenosyl moiety serves as the molecular anchor for cofactor binding.

The second class is N-mustard analogs of AdoMet such as 5'-(diaminobutyric acid)-N-iodoehtyl-5'-deoxy-8-azido-adenosine or 5'-[(N-iodoethyl)propargylamino]-5'-deoxy-adenosine (Zvag et al., (2006) *J. Am. Chem. Soc.* 128, 2760-2761). These compounds are structurally and mechanistically similar to the aziridine analogs. They undergo methyltransferase-directed coupling of the whole cofactor molecule to a target adenine or cytosine residue in DNA via its iodoethyl group (the coupling is thought to occur via transient formation and opening of an aziridine ring). These analogs contain the anchoring adenosyl moiety and may contain the homoserine side chain as well. A number of two-step labeling/conjugation methods have been proposed using this approach. For example, U.S. Pat. No. 7,465,544, publ. 2007, discloses reacting groups that are ligatable to the cofactor analogs and can also be used as detectable labels.

The third class of AdoMet analogs contain only replacements of the methyl group with an extended allyl (—CH$_2$CH═CH$_2$) or propargyl (—CH$_2$C≡CH) group bound at the activating sulfonium center. These cofactors are named doubly-activated AdoMet analogs since they bear an activating double or triple bond in beta-position to the transferable carbon unit (Dalhoff et al., (2006) *Nat. Chem. Biol.* 2, 31-32). The adenosyl and homocysteine moieties are the molecular anchors for cofactor binding, and only part of its molecule (the sulfonium bound activated side chain) is transferred onto a target molecule. These cofactors can be used for methyltransferase-directed derivatization and two-step labeling of plasmid DNA (Lukinavicius et al., (2007) *J. Am. Chem. Soc.* 129, 2758-2759). These analogs are claimed in WO 2006/108678, publ. 2006, and provide the possibility for transferring smaller linear groups (part of the molecule) onto target biomolecules by methyltransferases, which can be used for labeling of DNA.

However, the labeling strategies that exploit the above cofactor analogs (including the doubly-activated cofactors) bear the following shortcomings:

1) The chemistries of the labeling reactions provide a limited selection with respect to the nature of groups attached to target biomolecules, especially small groups. The minimal transferred unit comprises an entire cofactor molecule in the case of N-adenosylaziridine or N-mustard analogs. For the doubly-activated cofactors, a minimal transferable moiety comprises a 3-carbon linear chain (allyl or propargyl) plus a functional group; however, typically, larger transferable units are used (Klimasauskas and Weinhold, (2007) *Trends Biotechnol.* 25, 99-104). This limits the applicability of the labeling reactions in such cases when minimal changes to a original biomolecules are required. Furthermore, besides the size limitations, applications of labeled biomolecules may impose certain structural requirements to the attached groups. For example, groups such as hydroxymethyl, 1-hydroxyethyl, 2-chloro-1-hydroxyethyl, 2-hydroxyethylthiomethyl cannot be transferred to cytosine DNA in a sequence-specific manner by any methods known to the prior art. Therefore, labeling methods that are able to attach even shorter moieties or those that expand the existing repertoire of linker/functional group combinations are highly desired.

2) All known types of AdoMet analogs are chemically complex and expensive to obtain (multi-step synthetic procedures including numerous purification steps are required (Pljevaljcic et al., (2003) *J. Am. Chem. Soc.* 125, 3486-3492; Pljevaljcic et al., (2004) *Methods Mol. Biol.* 283, 145-161; Lukinavicius et al., (2007) *J. Am. Chem. Soc.* 129, 2758-2759). The availability of labeling reagents may be thus limited due to their high cost.

3) The N-adenosylaziridine and doubly-activated AdoMet analogs are quite unstable chemically and thus exhibit short half-lifes under physiological conditions (C. Dalhoff, (2005) *Dokt. Diss, Aachener Beiträger zur Chemie*, Bd. 63; ISBN 3-86130-767-7). This may limit the productive incubation time of a labeling reaction to 1-2 hours. They also need to be stored in special buffers at low temperature (−20° C. to −70° C.). These limitations may be critical in applications, when labeling reagents need to be stored for certain periods of time at ambient temperature or unfrozen (in a refrigerator).

4) All previously known labeling reactions make use of cofactor analogs which form high affinity complexes with directing methyltransferases. Therefore the labeling reactions produce inhibitory products—either tightly bound substrate-cofactor conjugates (with the N-aziridine and N-mustard analogs), or the natural reaction product S-adenosyl-L-homocysteine (with doubly-activated cofactors). These products will remain unproductively bound to the methyltransferase, which may limit enzymatic turnovers of the labeling reaction to a single or just a few turnovers, respectively (Klimasauskas and Weinhold, (2007) *Trends Biotechnol.* 25, 99-104). This in turn may reduce the efficiency of the reaction and require higher amounts of labeling reagents (cofactor analog and methyltransferase) and extended incubation times.

5) The use of the doubly-activated cofactors with long transferable side chains often is inefficient with wild type methyltransferases due to increased steric bulk of the transferable side chain. One solution to this problem is a steric engineering of the cofactor binding pocket in a directing methyltransferase by site-directed mutagenesis (Lukinavicius et al., (2007) *J. Am. Chem. Soc.* 129, 2758-2759). However it is not clear if this approach will be successful for other enzymes, since successful engineering examples come only from a single class methyltransferase enzymes. This may limit the applicability of the method, especially its expansion to other classes of AdoMet-dependent methyltransferases as directing enzymes.

Therefore, techniques that (i) permit sequence-specific covalent attachment of short functional groups ($C_1$-$C_4$ chains) onto target biomolecules and (ii) use chemically simple and inexpensive compounds are desired.

SUMMARY OF THE INVENTION

These problems can be overcome by providing the embodiments characterized in the claims 1-19 of the present invention.

The main idea of the present invention relates to the use of covalent coupling of non-cofactor compounds, represented by formulas (I) or (II)

wherein R and Z are independently selected from H, D, $C_1$-$C_{12}$-alkyl, preferably $C_1$-$C_4$-alkyl, alkenyl, alkinyl, phenyl or -LX, wherein X represents a functional group or a reporter group attached via a linker group L, and QH is selected from —SH, —SeH, —NHNH$_2$ or —ONH$_2$, for a targeted modification or derivatization of a biomolecule by covalent coupling to the biomolecule in the presence of a directing methyltransferase.

R is preferably selected from the group, comprising hydrogen, —CH$_3$, —CH$_2$CH$_3$, —CH$_2$Cl, —CH$_2$N$^+$(CH$_3$)$_3$Cl$^-$, —CH$_2$OCH$_2$C$_6$H$_5$, QH is preferably —SH and Z is selected from the group, comprising —CH$_2$CH$_2$OH, —CH$_2$CH(CO$_2$H)NH$_2$, –5'-adenosyl.

Such compounds, in the presence of a methyltransferase, were found to be selectively coupled to a specific locus on a biomolecule that is the natural target of the directing methyltransferase. One example of substrate-activating methyltransferases is pyrimidine-5 specific methyltransferases, which catalyze the transfer of a methyl group to the 5 position of cytosine or uracil residues in DNA, RNA or free nucleotides by making a transient covalent bond to the 6 position of the pyrimidine ring.

The present invention covers a method for targeted modification of a biomolecule comprising incubation of the biomolecule with a compound (I) or sequentially with compounds (I) and (II) of the present invention in the presence of a methyltransferase under conditions that allow for the coupling of the compound(s) onto the target molecule.

This invention also relates to a method for targeted labeling of a biomolecule and for targeted derivatization of a biomolecule, both characterised by incorporating of the step of targeted modification of a biomolecule according to the present invention.

This invention also relates to a method for detecting unmethylated target sites in a biomolecule, involving modification of the biomolecule by covalent coupling non-cofactor compound (I) or sequentially compound (I) and (II) in the presence of directing methyltransferase onto said biomolecule.

Finally, the present invention relates to a kit comprising a methyltransferase and non-cofactor compounds (I) or compounds (I) and (II) for performing any of the methods above.

DESCRIPTION OF THE DRAWINGS

To illustrate the main characteristic features of the present invention this description contains.

DETAILED DESCRIPTION OF THE INVENTION

Figure 1:
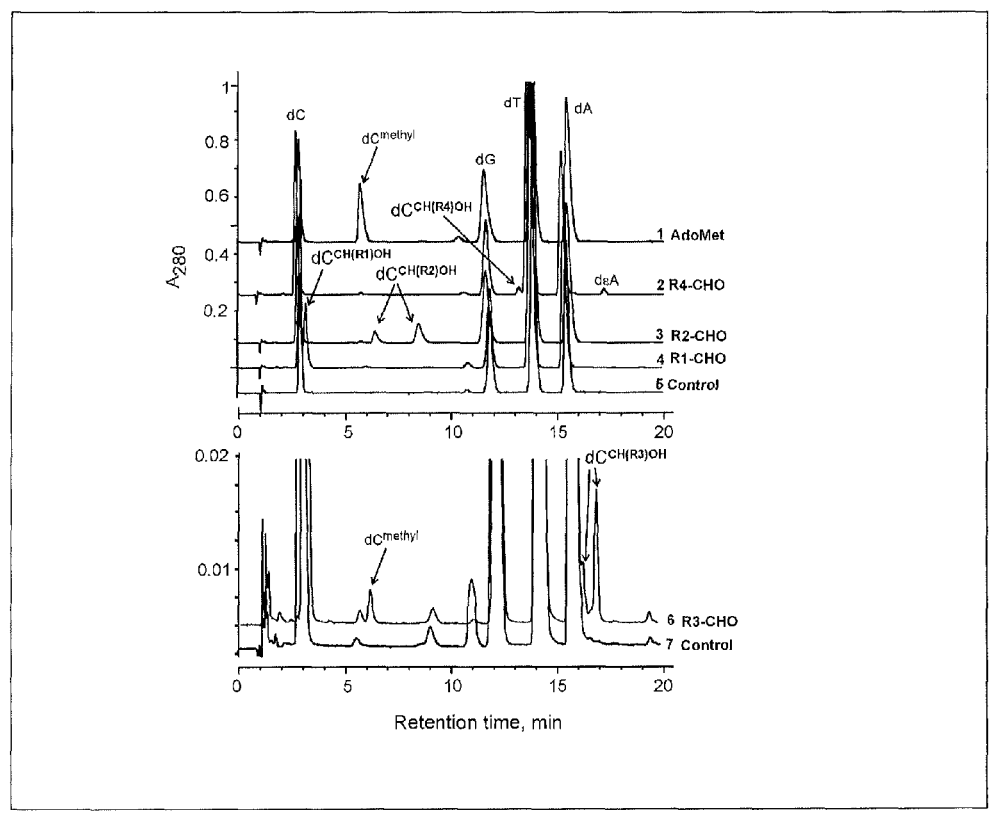
FIG. 1: Reversed-phase HPLC analysis of enzymatically fragmented duplex oligodeoxynucleotides obtained after treatment with M.HhaI and compound (I). 13 µM I:II duplex was incubated, in the presence of 15 µM M.HhaI, with 13 mM R1-CHO (trace 4), 800 mM R2-CHO (trace 3), 200 mM R3-CHO (trace 6), 200 mM R4-CHO (trace 2) or 200 µM AdoMet (trace 1) for 1 hour at room temperature. Control reactions (trace 5 and 7) contained lacked neither exogenous reagent nor M.HhaI. dεA in trace 2 denotes 1,N6-etheno-2'-deoxyadenosine. The HPLC elution buffer A was 20 mM ammonium formate pH 3.5. Arrows point at peaks corresponding to new modification products. The chemical group —CH(R)OH is attached to the C5 position of dC, where R1=-H, R2=-CH$_3$, R3=-CH$_2$CH$_3$, R4=-CH$_2$Cl.

The major object of the present invention is the use of non-cofactor compounds, represented by formulas (I) or (II)

wherein R and Z are independently selected from H, D, $C_1$-$C_{12}$-alkyl, preferably $C_1$-$C_4$-alkyl, or -LX, wherein X represents a functional group or a reporter group attached via a linker group L, and QH is selected from —SH, —SeH, —NHNH₂ or —ONH₂, for a targeted modification or derivatization of a biomolecule by covalent coupling to the biomolecule in the presence of a directing methyltransferase.

The general principle of sequence-specific modification of a target molecule according to the present invention can be understood from the Scheme 1 below which shows possibilities of targeted modification of cytosine residues in DNA in the presence of DNA cytosine-5 methyltransferases (MTase).

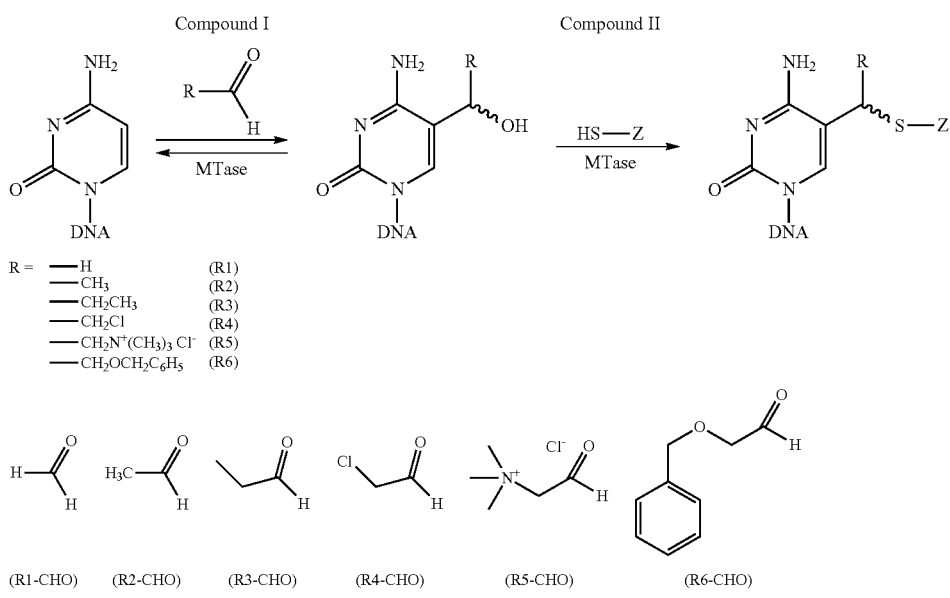

Z = —CH$_2$CH$_2$OH (Z1)
—CH$_2$CH(CO$_2$H)NH$_2$ (Z2)
-5'-adenosyl (Z3)
—CH$_2$CH$_2$NH$_2$ (Z4)
—CH$_2$CH(OH)CH(OH)CH$_2$SH (Z5)
—OH (Z6)

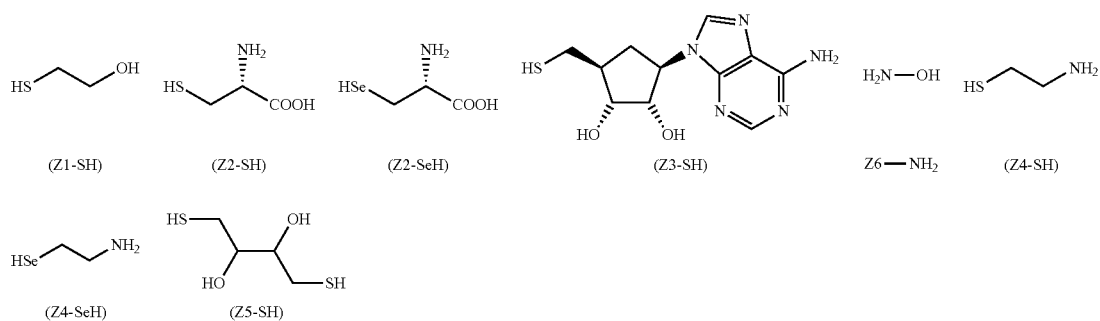

(Z1-SH) (Z2-SH) (Z2-SeH) (Z3-SH) Z6—NH$_2$ (Z4-SH)

(Z4-SeH) (Z5-SH)

This new modification reaction offers a number of advantages over the above described methods for sequence-specific modification of biomolecules:
- the compounds of the present invention provide new possibilities for introducing diverse functionalities and reporters into DNA (especially small groups) that are not accessible using the previously described AdoMet analogs of prior art;
- the compounds of the present invention are chemically simple, much less expensive;
- these compounds are much more stable, and due to their low cost and availability can be readily supplied in large amounts if required;
- the coupling reactions produce no inhibitory side products that could make a tight inhibitory complex with a methyltransferase;
- due to their lower complexity and bulk, the compounds of the present invention require much less, if any, modification of the directing methyltransferases.

In support of the novelty and inventive step of the present invention it should be noted:

1) The compounds represented by formula (I) and (II) do not resemble any known class of AdoMet analogs and are not bona fide cofactors of AdoMet-dependent methyltransferases; they lack any anchor moiety such as adenosyl or homoserine, which assist in the formation of a discrete specific complex with methyltransferases (Pignot et al., (2000) *Eur. J. Org. Chem.* 549-555; Merkiene and Klimasauskas (2005) *Nucleic Acids Res.* 33, 307-315; Klimasauskas and Weinhold, (2007) *Trends Biotechnol.* 25,99-104). The reactive groups in compounds represented by formula (I) and (II) (aldehyde and thiol, respectively) are distinct from all previously described clases of AdoMet analogs (aziridine, haloethylamine, alkylsulfonium).

2) The primary reaction described in the present invention is novel and is not obvious to the skilled person, since the reaction type (nucleophilic addition) is different from the S$_N$2 transfer (nucleophilic substitution) naturally used by all methyltransferases including reactions of the known AdoMet analogs. The secondary condensation reaction with nucleophiles such as thiols (QH=SH) is a completely new reaction in DNA.

3) The functionalities produced in DNA (5-alpha-hydroxyalkylcytosine, and 5-alkylthiomethylcytosine) are novel and cannot be introduced in a sequence-specific manner by any other known means. 5-hydroxymethylcytosine (HMC) can be incorporated into DNA randomly using a DNA polymerase and the corresponding nucleoside 5'-triphosphate (Kutter and Wiberg (1969) *J. Virol.* 4, 439-453), or can be incorporated in specific positions of short DNA strands by de novo chemical synthesis of oligodeoxyribonucleotides (Tardy-Planechaud et al., (1997) *Nucleic Acids Res.* 25, 553-558). Incorporation of HMC in specific sequences of long natural DNA can only be achieved using the methods disclosed by the present invention.

In a preferred embodiment of the present invention, R comprises hydrogen, D, —CH$_3$, —CH$_2$CH$_3$, —CH$_2$Cl, —CH$_2$N$^+$(CH$_3$)$_3$ or —CH$_2$OCH$_2$C$_6$H$_5$ and Z comprises —CH$_2$CH$_2$OH, —CH$_2$CH(CO$_2$H)NH$_2$ or -5'-adenosyl. However it is obvious to the person, skilled in the art, that R might be easily extended to C$_1$-C$_{12}$ alkyl, alkenyl, alkynyl, phenyl or LX, and Q—to cover at least —SeH, —NHNH$_2$ or —ONH$_2$.

In preferred embodiments of the present invention L is —CH$_2$— or —CH$_2$OCH$_2$— in compound I and L is —CH$_2$CH$_2$—, —CH$_2$CH(CO$_2$H)— or -5'-adenosyl in compound II, but it is understandable to the skilled person, that L is also covering another suitable linker groups, such as combination of linear, cyclic or aromatic moieties optionally connected with —NHCO—, —O—, —S— connectors, (poly)ethyleneglycol chains —(CH$_2$CH$_2$O)$_n$— n=1-100, etc.

Four general approaches (A-D) for sequence-specific derivatization and labeling of DNA are outlined in Scheme 2 below.

Scheme 2: General approaches (A-D) for sequence-specific methyltransferase-directed derivatization and labeling of DNA using compounds (I) and (II) according to present invention.
A
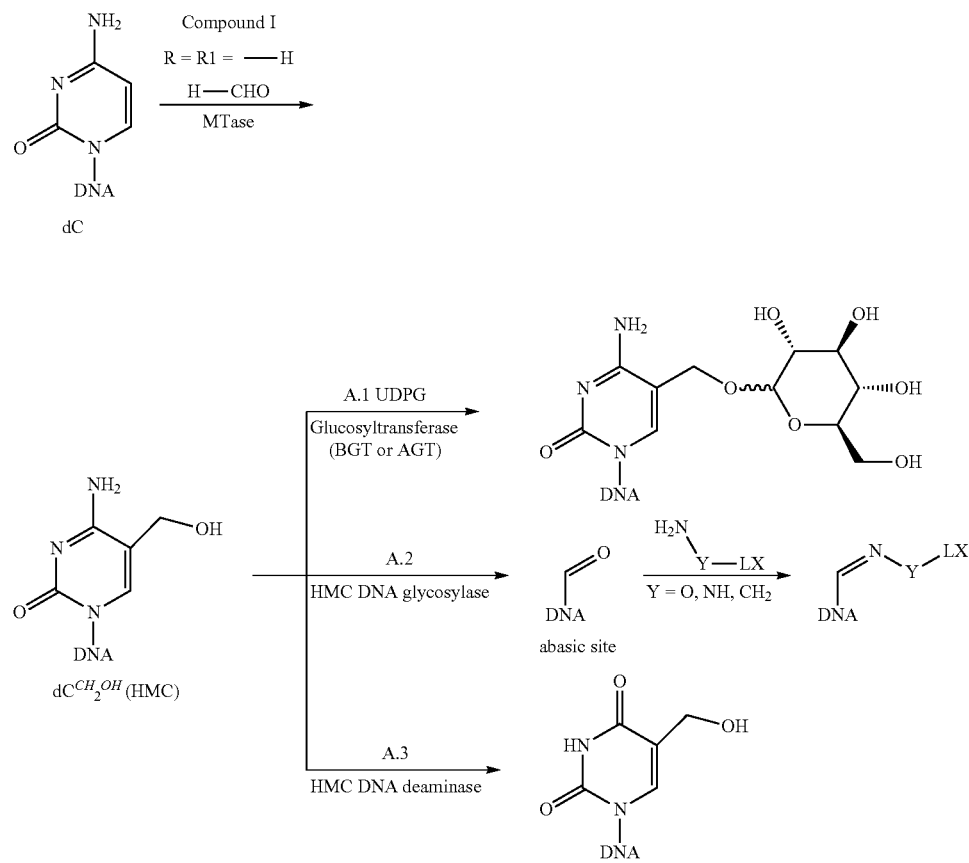
B
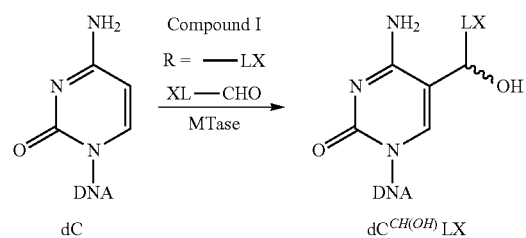
C
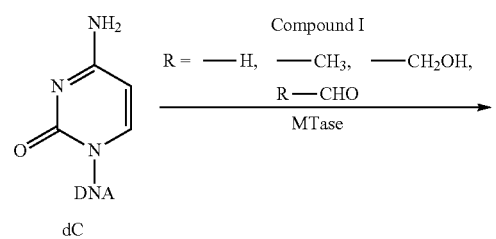

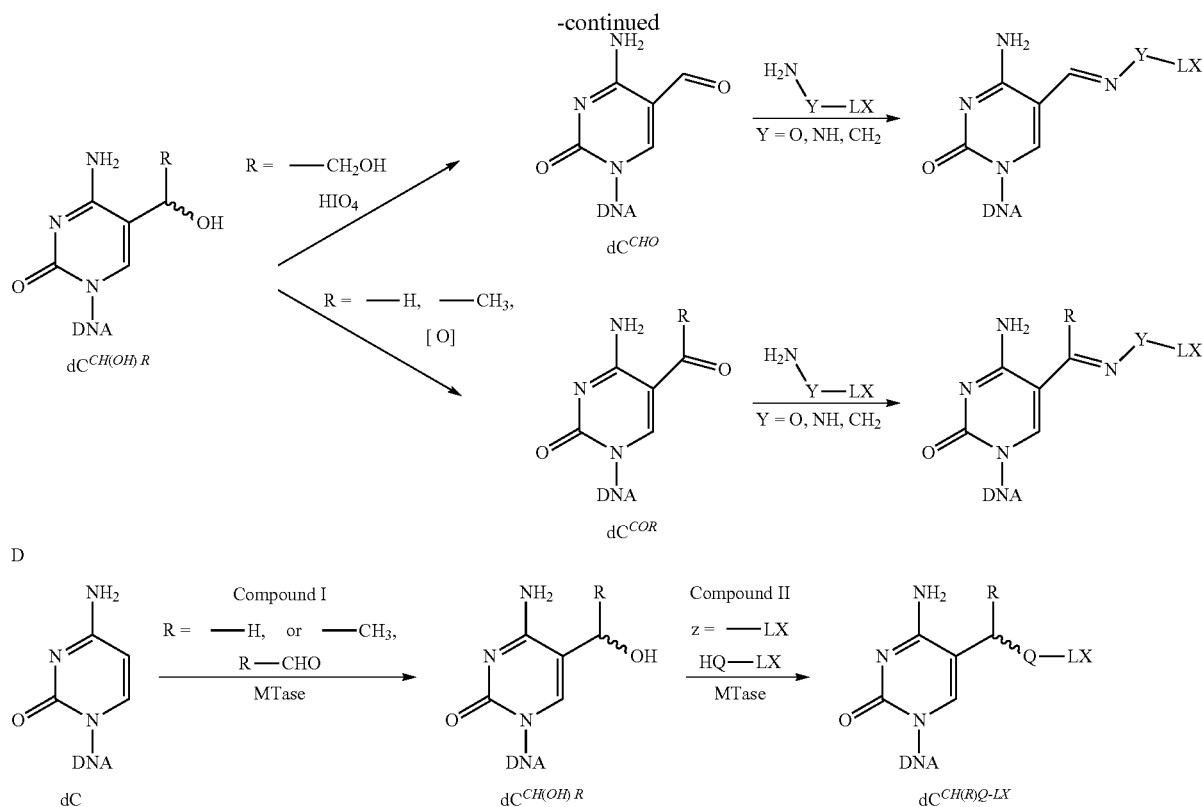

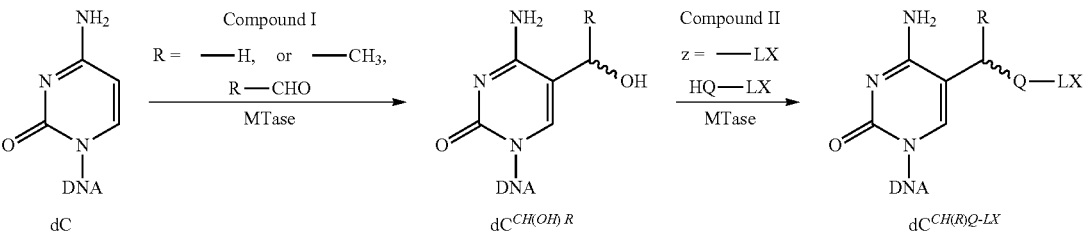

Approach A: Treatment of DNA with formaldehyde (Compound (I), R=H) in the presence of a directing DNA cytosine-5 methyltransferase permits sequence-specific production of 5-hydromethylcytosine (hmC) in DNA. This unique modification of DNA can be used for many useful applications. First, this modification can be useful if formaldehyde is isotopically labeled, for example with $^{14}C$, $^{13}C$, $^{3}H$ (T), $^{2}H$ (D) or $^{18}O$ nuclei. The $^{14}C$, $^{3}H$ nuclei are radioactive and can be detected by beta-emission counters, autoradiography or fluorography. Incorporation of $^{13}C$ and/or $^{2}H$ nuclei in DNA can be used for NMR experiments of DNA molecules containing the natural abundance of isotopes. 5-hydromethyl groups can be reduced with $NaBH_4$ or $Na(CN)BH_3$ (or their isotopically modified versions) to 5-methyl groups yielding a variety of isotopic combinations suitable for NMR analyses of biomolecules. All of the above nuclei can also be used for isotopic labeling of biomolecules to be analyzed by mass spectrometry.

In addition, hmC residues in DNA can be further modified using several enzymatic systems. For instance:

1) glucosyltransferases BGT and AGT isolated from T4 bacteriophages and other similar enzymes can catalyze the transfer of a glucose moiety from the uridine-diphosphoglucose (UDPG) cofactor (Lariviere and Morera (2002) *J. Mol. Biol.* 324, 483-490; Lariviere et al., (2005) *J. Mol. Biol.* 352, 139-150); such glucosylated residues can be detected using specific antibodies (Ignashov, (1976) *Mol. Biol. (Mosk)*,10, 682-685). 2) a hmC-specific glycosylase found in mammalian cells can excise the hmC base producing an abasic site in DNA. Such abasic lesions can serve as strand cleavage sites upon treatment with piperidine, or can be derivatized with aldehyde-specific compounds (Cannon et al., (1988) *Biochem. Biophys. Res. Commun.* 151, 1173-1179). 3) several reports suggest the existence of cellular enzymes that catalyze hydrolytic deamination of hmC into 5-hydroxymethyluracil in DNA (Rusmintratip and Sowers (2000) *PNAS* 26, 14183-14187). Treatment with such an enzyme and subsequent sequencing could reveal the positions of the hmC residues in DNA by comparing the readings of T and C tracks in the modified and unmodified DNA samples (Scheme 2A).

Approach B. Compound (I) can be prepared to carry a suitable functional group or reporter group X attached via a linker moiety L (R=-LX). Such a compound (I) can be coupled to the target molecule in the presence of a directing methyltransferase (Scheme 2B). The chemical reactive group X can then be used for covalent ligation with a suitable compound carrying a reporter group (two-step labeling, see below), or can be treated with another reagent to initiate a secondary internal modification in the target DNA molecule at or around the modified base. Useful secondary modifications include the change of the base-pairing properties, base excision, strand cleavage or inter-strand cross-link.

Approach C. Treatment with acetaldehyde or formaldehyde (Compound (I), R=$CH_3$, or H) in the presence of a directing DNA cytosine-5 methyltransferase permits sequence-specific production of 5-(1-hydroxyethyl) or 5-hydroxymethyl groups, respectively, at the target cytosine residues in DNA. Secondary treatment of the modified DNA with a mild oxidation reagent such as $MnO_2$ (LaFrancois et al. (1998) *Chem. Res. Toxicol.*, 11, 75-83) could convert them into 5-acetyl or 5-formyl groups, respectively. Alternatively, treatment with glycolaldehyde (Compound (I), R=—$CH_2OH$) in the presence of a directing methyltransferase permits sequence-specific production of 5-(1,2-dihydroxyethyl) groups at the target cytosine residues in DNA whereby producing a 1,2-diol functional group (see below for chemoligation reactions involving 1,2-diols). Secondary treatment of the modified DNA with periodic acid ($HIO_4$) or lead tetracetate (Pb(OAc)$_4$) will lead to an oxidative diol cleavage (House H. O. *Modern synthetic reactions*, 2$^{nd}$ ed., W. A. Benjamin, NY, 1972) yielding 5-formyl groups. Since carbonyl groups are absent in natural DNA, the 5-acetyl or 5-formyl groups can be used for selective chemoligation with compounds carrying primary amines, hydrazine, hydroxylamine or 1,2-aminothiol groups (Scheme 2C).

Approach D. Sequential treatment of DNA with formaldehyde or acetaldehyde (Compound (I), R=H or CH$_3$) and then with a suitable compound (II) (Z=LX wherein LX comprises a chemical reactive group or a reporter group X attached via a linker L) in the presence of a directing DNA cytosine-5 methyltransferase permits sequence-specific coupling of the two compounds to give incorporation of the LX group via a thiomethyl anchor (when QH=—SH) at the target cytosine residues (Scheme 2D). The chemical reactive group X can then be used for covalent ligation with a suitable compound carrying a reporter group (two-step labeling, see below). Successful implementation of this approach is demonstrated in Example 18. The chemical reactive group LX can also be treated with another reagent to initiate a secondary internal modification in the target DNA molecule at or around the modified base. Useful secondary modifications include alterations of base-pairing, base excision, strand cleavage or an inter-strand cross-link. When QH=SeH, a similar work out will lead to targeted incorporation of the LX group via a selenomethyl anchor into a biomolecule. The chemical reactive group X can then be used for covalent ligation with a suitable compound carrying a reporter group. [Since selenides can be readily oxidized with subsequent cleavage of the Se—C bond, the selenomethyl anchor can thus be used as a conditionally cleavable covalent linker in affinity purifications of labeled biomolecules.] On the other hand, the presence of Se in the anchoring group can also be used for phasing X-ray diffraction data during crystallographic determination of biomolecular structure.

Correspondingly, a method of targeted derivatization of a biomolecule proposed comprises primary modification of the biomolecule in the presence of methyltransferase with non-cofactor compound (I), or sequential modification with compound (I) and then with compound (II) according to present invention, followed by a) covalent ligation with a compound carrying a chemical reactive group that can be covalently ligated with a functional group X in the modified biomolecule; or b) secondary chemical modification of the biomolecule at the modified target base, wherein secondary modification involves reactions of other attached groups besides the functional group X; or c) secondary internal modification of the biomolecule comprising a further chemical reaction of the attached functional group X with the target base or nearby (adjacent) moieties; or d) enzymatic secondary modification of the 5-hydroxymethylcytosine residue in the modified biomolecule, wherein said primary modification of the biomolecule is achieved by the method according to present invention.

In this method of targeted derivatization said step b) of the secondary chemical modification of the biomolecule at the modified target base comprises a treatment with a mild oxidation reagent, such as MnO$_2$ or periodic acid, followed by further selective chemoligation of the formed carbonyl group with compounds carrying a carbonyl-reactive group, selected from primary amines, hydrazine, hydroxylamine or 1,2-aminothiol.

The corresponding step c) of the secondary internal modification of the biomolecule comprises a further chemical reaction of the attached functional group X with the target base or nearby moieties, leading to changes of the base-pairing properties of the target base, excision of the target base, strand cleavage or interstrand cross-link in the modified biomolecule by the techniques known in the art.

Preferred embodiments of step d) of enzymatic secondary modification of the 5-hydroxymethylcytosine residue in the modified biomolecule are performed by any of the following:

i) treatment with an UDP-glucose:DNA D-glucosyltransferase and UDP-glucose or derivatives thereof leading to targeted incorporation of D-glucose or a derivative thereof into the biomolecule; or ii) treatment with a 5-hydroxymethylcytosine-DNA deaminase, converting 5-hydroxymethylcytosine into 5-hydroxymethyluridine, which conversion is detectable by DNA sequencing; or iii) treatment with a 5-hydroxymethylcytosine-DNA glycosylase, producing an abasic site in the modified DNA strand which may be further processed using other techniques known in the art.

Further development of the method of targeted derivatization proposed is a method for targeted labeling a biomolecule comprising modification of the biomolecule according to the present invention, accompanied by incorporation of a group that is suitable as a label and that allows for the identification of the labeled biomolecules among other unlabeled molecules.

In a preferred embodiment of the present invention sequence-specific labeling of DNA was achieved by DNA methyltransferase-directed sequential coupling of compound (I) (aldehyde) and then compound (II) (thiol) followed by chemo-selective ligation with an e.g. fluorescent label, such as amine-reactive fluorescent label.

Scheme 3: Sequence-specific labeling of DNA using sequential coupling of compound (I), (R1-CHO) and compound (II), (Z2-SH) in the presence of a DNA methyltransferase (M•HhaI).

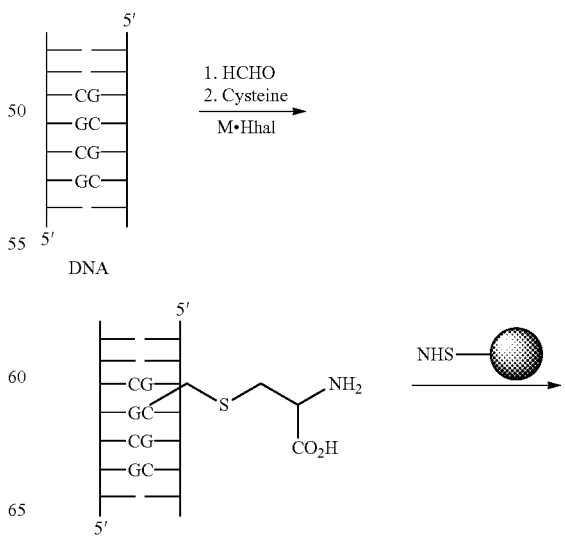

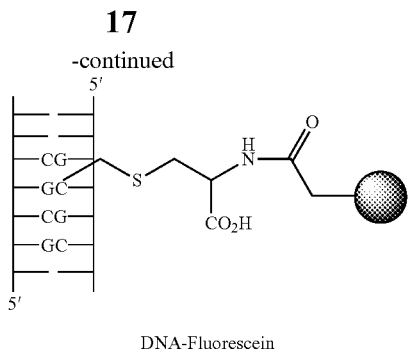

DNA-Fluorescein

Scheme 3 above demonstrates the principle of such sequence-specific labeling of DNA exemplified (see Example 18) by sequence-specific fluorescence labeling of plasmid DNA achieved by (i) sequential treatment of DNA with formaldehyde and L-cysteine in the presence of the HhaI methyltransferase, followed by (ii) amino-selective ligation with a fluorescein-NHS ester.

In the preferred embodiment of the present invention, (a) the compound of formula (I) of the present invention or a subsequent derivative thereof contains a fluorescent label; and (b) unmethylated targets sites are detected by the presence of fluorescence in said nucleic acid molecule (as in Example 18).

In another preferred embodiment of the present invention, the label of said detectable compound is detected by (a) an antibody specifically binding to the label of said detectable compound or by (b) avidin or streptavidin specifically binding to the label of said detectable compound.

As mentioned, numerous ways to achieve targeted labeling or targeted derivatization of biopolymers can be realized according to present invention. For this purpose a compound (I) or a compound (II) should typically contain a chemical moiety LX (R=LX or Z=LX), wherein X comprises a functional group or a reporter group that is attached via a linker group L.

Many chemo-selective ligations defining the reactive groups X are available for attaching a label to the modified biomolecule in aqueous solution. Classical ligations (Garman, (1997) Non-radioactive labeling: A practical introduction, Academic Press) involve primary amino groups which can be reacted with amine reactive groups like N-hydroxysuccinimidyl ester, acyl azide, acyl nitrile, acyl chloride, pentafluorophenyl ester, thioester, sulfonyl chloride, isothiocyanate, imidoester, aldehyde or ketone leading to stable amides, sulfonamides, thioureas, imidates or imines, which can be reduced to stable secondary amines. Thiols specifically react with haloacetamides, maleimides, aziridines or other thiols leading to thioether or disulfide linkages and 1,2-diols can be modified with arylboronic acids. Hydrazines or hydroxylamines can be condensed with aldehydes or ketones leading to hydrazones or oximes. 1,2-Aminothiols selectively react with aldehydes or thioesters to form thiazolidines (e.g. N-terminal cysteine residues of polypeptides, Liu and Tam, (1994) *Proc. Natl. Acad. Sci. USA* 91, 6584-6588) or stable amide bonds (e.g. N-terminal cysteine residues of polypeptides, native chemical peptide ligation, Dawson et al., (1994) *Science* 266, 776-779); azides can be reacted with alkynes (Huisgen 1,3-dipolar cycloaddition, Lewis et al. (2002), *Angew. Chem. Int*. Ed. 41, 1053-1057) or with phosphane esters (Staudinger ligation, Saxon and Bertozzi, (2000) *Science* 287, 2007-2010) to form 1,2,3-triazoles or amides; Diels-Alder cycloadditions between activated dienes and dienophiles (e.g. furanes and maleimides, Graham et al., (2002) *Tet. Lett*. 4785-4788) are feasible in aqueous solution. Other modern palladium-catalyzed cross-coupling reactions between arylhalides and terminal alkynes (Sonogashira coupling, Casalnuova and Calabrese, (1990) *J. Am. Chem. Soc*. 112, 4324-4330; Dibowski and Schmidtchen, (1998) *Angew. Chem. Int. Ed*. 37, 476-478; Bong and Ghaderi, (2001) *Org. Lett*. 3, 2509-2511) or between arylhalides and arylboronic acids (Suzuki coupling, Casalnuova and Calabrese, (1990) *J. Am. Chem. Soc*. 112, 4324-4330; DeVasher et al., (2004) *J. Org. Chem*. 69, 7919-7927) yielding arylalkynes or biaryls could be used. Additionally, copper-catalyzed alkyne coupling reactions between terminal haloalkynes and terminal alkynes or terminal silylalkyne leading to conjugated diynes can be performed in aqueous solution. Finally, fluorogenic derivatization reagents like 4-halo-7-nitrobenzofurazan, N-methylisatoic anhydride or activated bimanes can be used to label transferred thiol, amino or hydroxyl groups directly.

Nucleic acids generally do not contain highly nucleophilic or electrophilic centers. Thus, besides the cycloadditions, palladium-catalyzed cross-coupling reactions or copper-catalyzed alkyne coupling reactions, many other reactions between nucleophiles and electrophiles with interchangeable reactive group X could be used for sequence-specific labeling of nucleic acids.

In the preferred embodiment of the present invention X comprises at least one functional group, selected from a primary amino group, a thiol group, a 1,2-diol group, a haloacetamide group, a maleimide group, an aldehyde group, a ketone group, an azido group, an alkyne group, a 1,3-diene function, a dienophilic function, an arylhalide group, a terminal alkyne group, an arylboronic acid group, a terminal haloalkyne group, a terminal silylalkyne group and a protected amino, thiol, 1,2-diol, hydrazino, hydroxyamino, aldehyde, ketone and 1,2-aminothiol group. For the purposes of labeling of biopolymers X also comprises heavy atoms or heavy atom clusters suitable for phasing of X-ray diffraction data, radioactive or stable rare isotopes, and a residue of a member selected from fluorophores, fluorescence quenchers, chromophores, affinity tags, spin labels (stable paramagnetic groups), groups containing radioactive or stable rare isotopes, groups containing heavy atoms suitable for phasing X-ray diffraction data, crosslinking agents, nucleic acids cleaving groups, haptens, nanoparticles and beads.

The present invention also relates to a method for detecting unmethylated target sites of a directing methyltransferase in a biomolecule, comprising: (a) modification of the biomolecule with non-cofactor compound (I) or sequentially with compound (I) and compound (II) in the presence of said methyltransferase; and (b) detecting whether the target sites of said methyltransferase have been modified with non-cofactor compound(s) or a derivative thereof, wherein modification of the target site of said methyltransferase is indicative of the presence of the unmethylated target site.

The term "detecting whether the target sites of said methyltransferase have been modified with the compound or a derivative thereof" means assessing whether the non-cofactor compound (I) or sequentially compounds (I) and (II) or derivatives thereof is attached to the biomolecule. Preferably, detection methods involve identifying the particular residue, within the target sequence of the methyltransferase, modified by non-cofactor compounds (I) or (II).

It has been observed by the inventors of the present invention that coupling of non-cofactor compound of formula (I) or (II) used in the present invention, at the acceptor site of the recognition sequence blocks DNA cleavage by restriction enzymes with an overlapping or the same recognition sequence. Blocking restriction enzyme cleavage, as used herein, means preventing the restriction enzyme from cutting the DNA strands (see Examples 14-17).

In yet another preferred embodiment of the present invention, (a) the non-cofactor compound of formula (I) or (II) used in present invention interferes with nucleic acid amplification at the recognition sites of the methyltransferase; and (b) unmethylated target sites are detected by testing whether amplification of the nucleic acid molecule at the recognition sites of the methyltransferase has been retarded. Retardation of amplification may be achieved by interfering with primer binding or with strand elongation during an amplification reaction.

During the methods of present invention, a step of nucleic acid sequencing may be performed. Any methods known in the art may be used for sequencing.

In a preferred embodiment of the present invention, PCR is real-time PCR. In another preferred embodiment of the present invention, nucleic acid amplification is carried out by real-time PCR.

In another preferred embodiment of the present invention, (a) nucleic acid molecules modified at the methyltransferase recognition sequence are purified by affinity purification; and (b) the compounds of formulas (I) or (II) used in the present invention or a derivative thereof contains an affinity tag.

In a preferred embodiments, the methods of present invention comprises after step of targeted modification of a biomolecules an additional step of sequencing the DNA molecule. Any methods known in the art may be used for sequencing.

Examples provided in the present invention (Example 8, FIG. 3) show that the compound of formula (I) of the present invention or a derivative thereof is added to a cytosine residue and cannot be added to a 5-methylcytosine residue in DNA.

In yet another preferred embodiment of the present invention, the identity of said DNA molecule is determined by DNA sequencing, hybridization, MALDI-TOF or analysis of nucleoside composition by enzymatic fragmentation and chromatography.

Finally, in one of preferred embodiments, the kit of the present invention comprises a methyltransferase and non-cofactor compounds (I) or compound (I) and (II) as defined in the present invention in separate containers and may further contain an information leaflet or instruction for use.

Compounds (I) and (II) can also be supplied in a chemically altered form such as modified with a protecting group, in an oligomeric or polymeric form that releases the compound(s) immediately or slowly when brought into a suitable milieu such as a methyltransferase buffer. For example aldehydes are known to exist as dimers (glycerol aldehyde dimer, glycol aldehyde dimer), trimers (formaldehyde trimer or 1,3,5-trioxane), polymers (paraform or paraformaldehyde) or protected forms (urotropin, mono- and diacetals, Schiff bases etc.). These compounds are slowly hydrolyzed in aqueous buffers (and faster under acidic conditions) to release corresponding aldehydes. Similarly, thiols exist in an oxidized form as disulfides or polysulfides etc., which easily convert to thiols under reducing conditions. These or similar chemically altered forms of compounds I and II can also be used for performing the modification reactions described in the present invention.

The present invention also relates to a kit containing both compound (I) and compound (II) as defined in the present invention and a methyltrasferase or diagnostic formulation(s) on the basis of above. The diagnostic formulation in one of the embodiments of present invention is a liquid composition. The preferred solvent of the diagnostic formulation is aqueous in nature. In addition, the formulation may contain other ingredients or carriers for modifying or maintaining the pH, osmolarity, viscosity, clarity, color, sterility, stability, rate of dissolution, or odor of the formulation. Similarly, the formulation may contain still other pharmacologically acceptable ingredients for modifying or maintaining the stability, rate of dissolution, release, or absorption of the diagnostic composition. Once the diagnostic formulation has been formulated, it may be stored in sterile vials as a solution, suspension, gel, emulsion, solid, or dehydrated or lyophilized powder. Such formulations may be stored either in ready to use form or requiring reconstitution immediately prior to use.

New derivatives formed in DNA upon treatment with compound (I) or sequentially with compounds (I) and (II) in the presence of a MTase, are also covered by the present invention.

In practice for preparation of a modified biomolecule according to the present invention the following steps are to be carried out:

a) combining (putting together) the biomolecule, a cofactor-free MTase and compound (I) in a suitable aqueous buffer (that is compatible with enzymatic activity of the methyltransferase);

b) incubation of the reaction at ambient temperature (or other temperature that is compatible with enzymatic activity of the methyltransferase) for a period of 5-120 min.;

c) stopping the reaction (by adding an inhibiting compound, diluting the reaction with a suitable solvent, cooling to a low temperature, or inactivating the methyltransferase by heating at a higher temperature for 5-20 min.);

d) isolation of a modified biomolecule as necessary.

For sequential modification of a biomolecule with compound (I) and then with compound (II), the following steps are to be carried out:

a) combining (putting together) the biomolecule, a cofactor-free MTase and compound (I) in a suitable aqueous buffer;

b) incubation of the reaction mixture at ambient temperature (or other temperature that is compatible with enzymatic activity of the methyltransferase) for a period of 5-120 min.;

c) (optional) stopping the reaction as above (by adding an inhibiting compound, diluting the reaction with a suitable solvent, cooling to a low temperature, or inactivating the methyltransferase by heating at a higher temperature for 5-20 min.);

d) (optional) isolation of the modified biomolecule;

e) adding compound (II) to the reaction mixture obtained in step b) (or combining the target biomolecule obtained in step d), a cofactor-free MTase and compound (II) in a suitable aqueous buffer);

f) incubation of the reaction mixture at ambient temperature (or other temperature that is compatible with enzymatic activity of the methyltransferase) for a period of 5-120 min.;

g) stopping the reaction (by adding an inhibiting compound, diluting the reaction with a suitable solvent, cooling to a low temperature, or inactivating the methyltransferase by heating at a higher temperature for 5-20 min.);

h) isolation of the sequentially modified biomolecule, if necessary.

Normally, directing MTases are supplied at near equimolar amounts with respect to biomolecular target sites; compounds (I) or (II) are typically used in millimolar concentrations.

Embodiments of the Invention

Represented below are specific examples of the embodiments of the present invention. The scope of the invention is only illustrated by these examples without being restricted to them.

Examples 1-12

Sequence-specific modifications of oligodeoxyribonucleotide duplexes with compound (I) or sequentially with compound (I) and compound (II) in the presence of the HhaI DNA cytosine-C5 methyltransferase.

Modification of the C5-position of cytosine with compounds (I) (R1-CHO=formaldehyde, R2-CHO=acetaldehyde, R3-CHO=propionaldehyde, R4-CHO=2-chloroacetaldehyde) or sequentially with compound I (R1-CHO=formaldehyde) and then with compound (II) (Z1-SH=2-mercaptoethanol, Z2-SH=L-cysteine, or Z3-SH=5'-thio-5'-deoxyadenosine) was first performed in the presence of the HhaI DNA cytosine-C5 methyltransferase (M.HhaI) using short duplex oligodeoxyribonucleotides. M.HhaI recognizes the 5'-GCGC-3' target site in DNA and naturally transfers the methyl group of S-adenosyl-L-methionine (SAM or AdoMet) to the C5 position of the inner cytosine residue (underlined). Following the enzymatic modification reactions, a duplex oligodeoxynucleotide was enzymatically fragmented to 2'-deoxynucleosides and analyzed by reversed-phase HPLC coupled with ESI-MS.

The duplex oligodeoxynucleotide 1:11 was produced by mixing equal molar amounts (150 µM) of complementary single-stranded oligodeoxyribonucleotide I (SEQ ID NO:1) (5'-TAATAATGCGCTAATAATAATAAT) and II (SEQ ID NO:2) (3'-TTATTACGCGATTATTATTATTA) in water, heating at 95° C. for 5 min and slow cooling to room temperature. Enzymatic modifications were performed by incubation of the duplex oligodeoxynucleotide I:II (13 µM) with Compound (I) (R1-CHO, 13 mM; R2-CHO, 800 mM and R3-CHO, R4-CHO, 200 mM) and M.HhaI (15 µM) in a buffer (200 µL, 50 mM MOPS, 50 mM MES pH 7.0, 1 mM Na2EDTA, 15 mM NaCl, 0.2 mg/ml bovine serum albumin, 5% glycerol) at 20° C. for 1 hour. Sequential coupling of compounds (II) and (I) was performed by first incubating the duplex oligodeoxynucleotide I:II (13 µM) with compound (I) (R1-CHO-13 mM) for 40 min as described above and then adding compound (II) to a final concentration as specified (Z1-SH (300 mM), Z2-SH (50 mM), Z3-SH (400 µM)), Z4-SH (12 m), Z5-SH (50 mM), Z2-SeH (1 mM), Z4-SeH (1.2 mM) or Z6-NH (50 mM) and incubating for 1 hour at room temperature.

DNA was then precipitated with 3 volumes of ethanol, dried and redissolved in buffer (100 µl, 10 mM Tris-HCl pH 7.5, 10 mM magnesium chloride, 1 mM Zinc acetate). Samples were then treated with Nuclease P1 (2 u, Sigma, Germany) for 2 hours at 60° C. and calf intestine alkaline phosphatase (30 u, Fermentas Life Sciences, Lithuania) overnight at 37° C. Obtained nucleosides were analyzed by reverse-phase HPLC (Discovery C18 75×2.1 mm, 3 µm column, equipped with a Supelguard Discovery C18 20×2.1 mm, 5 µm precolumn, Supelco, Germany) coupled with a mass spectrometric detector (HP 1100 series ESI-MS equipped with singe quadruple). Compounds were eluted with a linear gradient of solvents A (20 mM ammonium formate pH 3.5 or 20 mM ammonium acetate pH 5.5) and B (80% aqueous methanol) at a flow of 0.3 ml/min at 30° C. as follows: 0-20 min, 0-20% B; 20-22 min, 20-100% B; 22-27 min, 100% B. Analytes were detected by an in-line diode array UV absorbance detector. UV absorbance spectra were acquired (190-400 nm wavelength interval) at peak maxima and solvent contributions were removed by subtracting background spectra before and after the peaks. For online mass spectrometric detection post-column mobile phase modification (equal co-flow of 96% methanol, 4% formic acid and 1 mM sodium hydroxide) was used to enhance the detection efficiency of 2'-deoxycytidine and its derivatives. Mass spectra were recorded in 50-600 m/z range in the positive ion mode. Ionization capillary voltage was 5000 V, fragmenter voltage was 100-120 V, drying gas temperature was 300-350° C. and flow rate was 10-12 l/min.

High-resolution mass spectra were acquired by analysis of corresponding HPLC fractions on a LTQ Orbitrap mass spectrometer (Thermo Electron) equipped with a Proxeon Nano-Spray ESI.

Example 1

Nucleoside composition analysis of a duplex oligodeoxyribonucleotide after treatment with formaldehyde in the presence of M.HhaI.

HPLC analysis of nucleoside composition of the modified duplex oligodeoxyribonucleotide (I:II) treated with formaldehyde (R1-CHO) revealed in addition to the natural nucleosides dC, dG, dT and dA a new product with a retention time of 3.3 min (elution buffer 20 mM ammonium formate pH 3.5) or 4.2 min (elution buffer 20 mM ammonium acetate pH 5.5). No such new product is observed in the absence of M.HhaI of formaldehyde. This new product was analyzed by coupled ESI-MS (m/z: 280 [M+Na]+, 164 [5-hydroxymethylcytosine+Na]+) and separately by HR-MS (m/z found: 258.1085; calculated for [M+H]+ $C_{10}H_{16}N_3O_5$: 258.1084). The observed masses and the derived UV absorption spectrum at pH 3.5 ($\lambda_{max}$=282 nm) are in agreement with the formation of 5-hydroxymethyl-2'-deoxycytidine $dC^{CH(OH)R1}$. Thus the compound R1-CHO is coupled to the C5-position of cytosine in DNA by M.HhaI. See FIG. 1, trace 4 and FIG. 2, trace 2.

Example 2

Nucleoside composition analysis of a duplex oligodeoxyribonucleotide after treatment with acetaldehyde and in the presence of M.HhaI.

HPLC analysis of nucleoside composition of the modified duplex oligodeoxyribonucleotide (I:II) treated with acetaldehyde (R2-CHO) revealed in addition to the natural nucleosides dC, dG, dT and dA a new product within 2 peaks in HPLC trace (two isomers of a chiral center at the a-carbon) with a retention time of 6.5 and 8.3 min (elution buffer 20 mM ammonium formate pH 3.5). These new products were analyzed by coupled ESI-MS (m/z: 294 [M+Na]+, 178 [5-(1-hydroxyethyl)cytosine+Na]+) and separately by HR-MS (m/z found: 272.1243; calculated for [M+H]+ $C_{11}H_{18}N_3O_5$: 272.1241). The observed masses and the derived UV spectrum at pH 3.5 ($\lambda_{max}$=282 nm) are in agreement with the formation of 5-(1-hydroxyethyl)-2'-deoxycytidine $dC^{CH(OH)R2}$. Thus the compound R2-CHO is coupled to the C5-position of cytosine in DNA by M.HhaI. See FIG. 1, trace 3.

Example 3

Nucleoside composition analysis of a duplex oligodeoxyribonucleotide after treatment with propionaldehyde in the presence of M.HhaI.

Figure 2:
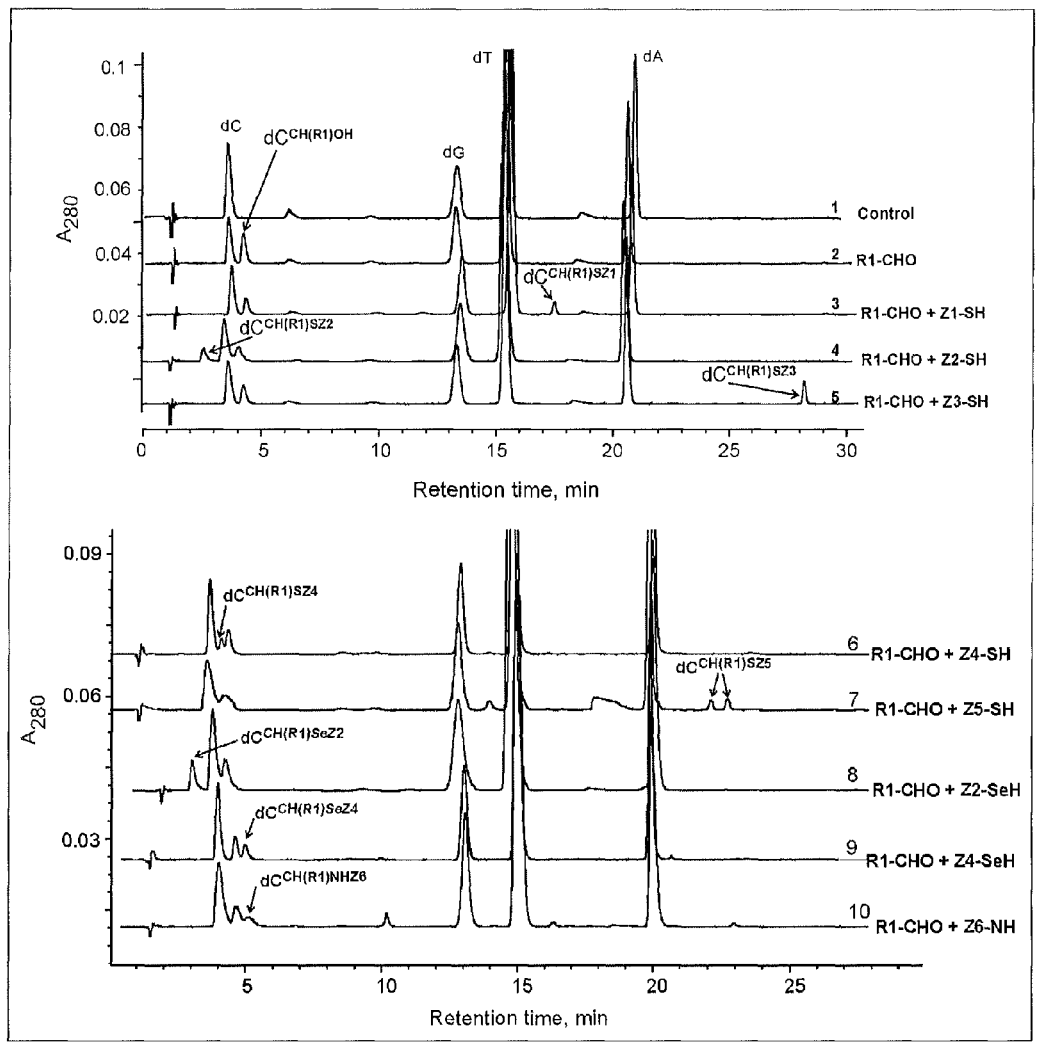
FIG. 2: Reversed-phase HPLC analysis of enzymatically fragmented duplex oligodeoxynucleotides obtained after treatment with M.HhaI, compound (I) and compound (II). 13 µM DNA duplex I:II was incubated, in the presence of 15 µM M.HhaI, with 13 mM R1-CHO for 40 min (trace 2) and then adding compound (II) to a final concentration of 300 mM Z1-SH (trace 3), 50 mM Z2-SH (trace 4) or 400 µM Z3-SH (trace 5) 12 mM Z4-SH (trace 6), 50 mM Z5-SH (trace 7), 1 mM Z2-SeH (trace 8), 1.2 mM Z4-SeH (trace 9) or 50 mM Z6-NH (trace 10) and incubating for 1 hour at room temperature. Control reaction (trace 1) contained lacked M.HhaI. The HPLC elution buffer A was 20 mM ammonium acetate pH 5.5. Arrows point at peaks corresponding to new modification products. The chemical groups —CH(R)OH and —CH(R)SZ are attached to the C5 position of dC, where R1=—H, Z1=—CH$_2$CH$_2$OH, Z2=—CH$_2$CH(CO$_2$H)NH$_2$, Z3=-5'-adenosyl.

HPLC analysis of nucleoside composition of the modified duplex oligodeoxyribonucleotide (I:II) treated with propionaldehyde (R3-CHO) revealed in addition to the natural nucleosides dC, dG, dT and dA a new product within 2 peaks in HPLC trace (two isomers of a chiral center at the a-carbon) with a retention time of 16.1 and 16.8 min (elution buffer 20 mM ammonium formate pH 3.5). These new products were analyzed by coupled ESI-MS (m/z: 308 [M+Na]+, 192 [5-(1-hydroxypropyl)cytosine+Na]+) and separately by HR-MS (m/z found: 286.1398; calculated for [M+H]+ $C_{12}H_{20}N_3O_5$: 286.1397). The observed masses are in agreement with the formation of 5-(1-hydroxypropyl)-2'-deoxycytidine $dC^{CH(OH)R3}$. Thus the compound R3-CHO is coupled to the C5-position of cytosine in DNA by M.Hhal. FIG. 1, trace 6.

Example 4

Nucleoside composition analysis of a duplex oligodeoxyribonucleotide after treatment with 2-chloroacetaldehyde in the presence of M.Hhal. HPLC analysis of nucleoside composition of the modified duplex oligodeoxyribonucleotide (I:II) treated with chloroacetaldehyde (R4-CHO) revealed in addition to the natural nucleosides dC, dG, dT and dA a new product with a retention time of 13.5 min (elution buffer 20 mM ammonium formate pH 3.5). This new compound was analyzed by coupled ESI-MS (m/z: 328 [M+Na]+, 212 [5-(1-hydroxy-2-chloroethyl)cytosine+Na]+) and separately by HR-MS (m/z found: 306.0852; calculated for [M+H]+ $C_{11}H_{17}N_3O_5Cl$: 306.0851). The observed masses and the derived UV spectrum at pH 3.5 ($\lambda_{max}$=284 nm) are in agreement with 5-(1-hydroxy-2-chloroethyl)-2'-deoxycytidine $dC^{CH(OH)R4}$. Thus the compound R4-CHO is coupled to the C5-position of cytosine in DNA by M.Hhal. See FIG. 1, trace 2.

Example 5

Nucleoside composition analysis of a duplex oligodeoxyribonucleotide after sequential treatment with formaldehyde and 2-mercaptoethanol in the presence of M.Hhal.

HPLC analysis of nucleoside composition of the modified duplex oligodeoxyribonucleotide (I:II) treated with 13 mM formaldehyde (R1-CHO) and 300 mM 2-mercaptoethanol (Z1-SH) revealed in addition to the natural nucleosides dC, dG, dT and dA two new products: one with the retention time of 5-hydroxymethyl-2'-deoxycytidine (Example 1) and another with a retention time of 16.8 min (elution buffer 20 mM ammonium acetate pH 5.5). This new product was analyzed by coupled ESI-MS (m/z: 340 [M+Na]+, 224 [5-(2-hydroxyethyl)thiomethylcytosine+Na]+) and separately by HR-MS (m/z found: 318.1118; calculated for [M+H]+ $C_{12}H_{20}N_3O_5S$: 318.1119). The observed masses are in agreement with 5-(2-hydroxyethyl)thiomethyl-2'-deoxycytidine $dC^{CH(R1)SZ1}$. Thus the compounds R1-CHO and Z1-SH are sequentially coupled to the C5-position of cytosine in DNA by M.Hhal. See FIG. 2, trace 3.

Example 6

Nucleoside composition analysis of a duplex oligodeoxyribonucleotide after sequential treatment with formaldehyde and L-cysteine in the presence of M.Hhal.

HPLC analysis of nucleoside composition of the modified duplex oligodeoxyribonucleotide (I:II) treated with 13 mM formaldehyde (R1-CHO) and then with 50 mM L-cysteine (Z2-SH) in the presence of M.Hhal revealed in addition to the natural nucleosides dC, dG, dT and dA two new products: one with the retention time of 5-hydroxymethyl-2'-deoxycytidine (Example 1) and another with a retention time of 2.7 min (elution buffer 20 mM ammonium acetate pH 5.5). This new products were analyzed by HR-MS (m/z found: 361.1176; calculated for [M+H]+ $C_{13}H_{21}N_4O_6S$: 361.1176). The observed mass is in agreement with 5-(2-amino-2-carboxyethyl)thiomethyl-2'-deoxycytidine $dC^{CH(R1)SZ2}$. Thus the compounds R1-CHO and Z2-SH are sequentially coupled to the C5-position of cytosine in DNA by M.Hhal. See FIG. 2, trace 4.

Example 7

Nucleoside composition analysis of a duplex oligodeoxyribonucleotide after sequential treatment with formaldehyde and 5'-thio-5'-deoxyadenosine in the presence of M.Hhal.

HPLC analysis of nucleoside composition of the modified duplex oligodeoxyribonucleotide (I:II) treated with 13 mM formaldehyde (R1-CHO) and then with 400 μM 5'-thio-5'-deoxyadenosine (Z3-SH) in the presence of M.Hhal revealed in addition to the natural nucleosides dC, dG, dT and dA two new products: one with the retention time of 5-hydroxymethyl-2'-deoxycytidine (Example 1) and another with a retention time of 27.5 min (elution buffer 20 mM ammonium acetate pH 5.5).

This new product was analyzed by coupled ESI-MS (m/z: 545 [M+Na]+, 429 [5-(5'-denosyl)thiomethyl-2'-deoxycytidine+Na]+) and separately by HR-MS (m/z found: 523.1718; calculated for [M+H]+ $C_{20}H_{27}N_8O_7S$: 523.1718). The observed masses are in agreement with 5-(5'-adenosyl)thiomethyl-2'-deoxycytidine $dC^{CH(R1)SZ3}$. Thus the compounds R1-CHO and Z3-SH are sequentially coupled to the C5-position of cytosine in DNA by M.Hhal. See FIG. 2, trace 5.

Example 8

Nucleoside composition analysis of a duplex oligodeoxyribonucleotide after sequential treatment with formaldehyde and cysteamine in the presence of M.Hhal.

HPLC analysis of nucleoside composition of the modified duplex oligodeoxyribonucleotide (I:II) treated with 13 mM formaldehyde (R1-CHO) and then with 12 mM cystamine (Z4-SH) in the presence of M.Hhal revealed in addition to the natural nucleosides dC, dG, dT and dA two new products: one with the retention time of 5-hydroxymethyl-2'-deoxycytidine (Example 1) and another with a retention time of 4.0 min (elution buffer 20 mM ammonium acetate pH 5.5).

This new product was analyzed by coupled ESI-MS (m/z: 339 [M+Na]+, 223 [5-(2-aminoethylthio)methylcytosine+Na]+). The observed masses are in agreement with 5-(2-aminoethyl)thiomethyl-2'-deoxycytidine $dC^{CH(R1)SZ4}$. Thus the compounds R1-CHO and Z4-SH are sequentially coupled to the C5-position of cytosine in DNA by M.Hhal. See FIG. 2, trace 6.

Example 9

Nucleoside composition analysis of a duplex oligodeoxyribonucleotide after sequential treatment with formaldehyde and 1,4-dithiothreitol(1,4-dithio-2,3-dihydroxy-butane) in the presence of M.Hhal.

HPLC analysis of nucleoside composition of the modified duplex oligodeoxyribonucleotide (I:II) treated with 13 mM formaldehyde (R1-CHO) and then with 50 mM 1,4-dithiothreitol (Z5-SH) in the presence of M.Hhal revealed in addition to the natural nucleosides dC, dG, dT and dA two new products: one with the retention time of 5-hydroxymethyl-2'-deoxycytidine (Example 1) and another with a retention time of 22.1 min and 22.8 min (two isomers) (elution buffer 20 mM ammonium acetate pH 5.5).

This new product was analyzed by coupled ESI-MS (m/z: 416 [M+Na]+). The observed masses are in agreement with 5-(2,3-dihydroxy-4-mercaptobutyl)thiomethyl-2'-deoxycytidine $dC^{CH(R1)SZ5}$. Thus the compounds R1-CHO and Z5-SH are sequentially coupled to the C5-position of cytosine in DNA by M.Hhal. See FIG. 2, trace 7.

Example 10

Nucleoside composition analysis of a duplex oligodeoxyribonucleotide after sequential treatment with formaldehyde and selenocysteine in the presence of M.Hhal.

HPLC analysis of nucleoside composition of the modified duplex oligodeoxyribonucleotide (I:II) treated with 13 mM formaldehyde (R1-CHO) and then with 50 mM selenocysteine (Z2-SeH) in the presence of M.Hhal revealed in addition to the natural nucleosides dC, dG, dT and dA two new products: one with the retention time of 5-hydroxymethyl-2'-deoxycytidine (Example 1) and another with a retention time of 3.1 min (elution buffer 20 mM ammonium acetate pH 5.5). This new product was analyzed by HR-MS (m/z found: 409.0621, calculated for $[M+H]+$ $C_{13}H_{21}N_4O_6Se$: 409.0621). The observed mass is in agreement with 5-(2-amino-2-carboxyethyl)selenomethyl-2'-deoxycytidine $dC^{CH(R1)SeZ2}$. Thus the compounds R1-CHO and Z2-SeH are sequentially coupled to the C5-position of cytosine in DNA by M.Hhal. See FIG. 2, trace 8.

Example 11

Nucleoside composition analysis of a duplex oligodeoxyribonucleotide after sequential treatment with formaldehyde and selenocysteamine in the presence of M.Hhal.

HPLC analysis of nucleoside composition of the modified duplex oligodeoxyribonucleotide (I:II) treated with 13 mM formaldehyde (R1-CHO) and then with 1.2 mM selenocysteamine (Z4-SeH) in the presence of M.Hhal revealed in addition to the natural nucleosides dC, dG, dT and dA two new products: one with the retention time of 5-hydroxymethyl-2'-deoxycytidine (Example 1) and another with a retention time of 5.0 min (elution buffer 20 mM ammonium acetate pH 5.5).

This new product was analyzed by coupled ESI-MS (m/z: 386 [M+Na]+). The observed masses are in agreement with 5-(2-aminoethyl)selenomethyl-2'-deoxycytidine $dC^{CH(R1)SeZ4}$. Thus the compounds R1-CHO and Z4-SeH are sequentially coupled to the C5-position of cytosine in DNA by M.Hhal. See FIG. 2, trace 9.

Example 12

Nucleoside composition analysis of a duplex oligodeoxyribonucleotide after sequential treatment with formaldehyde and hydroxylamine in the presence of M.Hhal.

HPLC analysis of nucleoside composition of the modified duplex oligodeoxyribonucleotide (I:II) treated with 13 mM formaldehyde (R1-CHO) and then with 50 mM hydroxylamine (Z6-NH) in the presence of M.Hhal revealed in addition to the natural nucleosides dC, dG, dT and dA two new products: one with the retention time of 5-hydroxymethyl-2'-deoxycytidine (Example 1) and another with a retention time of 5.0 min (elution buffer 20 mM ammonium acetate pH 5.5) in agreement with the formation of 5-hydroxylaminomethyl-2'-deoxycytidine $dC^{CH(R1)NHZ6}$. Thus the compounds R1-CHO and Z6-NH are sequentially coupled to the C5-position of cytosine in DNA by M.Hhal. See FIG. 2, trace 10.

As it is demonstrated above, the method of present invention was effective for obtaining new products, such as indicated in Table 1 below.

TABLE 1

| Exogenous reagent(s) | Reaction product | | |
|---|---|---|---|
| | Designation | Formula | Name |
| R2—CHO | $dC^{CH(R2)OH}$ | $C_{11}H_{17}N_3O_5$ | 5-(1-hydroxyethyl)-2'-deoxycytidine |
| R3—CHO | $dC^{CH(R3)OH}$ | $C_{12}H_{19}N_3O_5$ | 5-(1-hydroxypropyl)-2'-deoxycytidine |
| R4—CHO | $dC^{CH(R4)OH}$ | $C_{11}H_{16}N_3O_5Cl$ | 5-(2-chloro-1-hydroxyethyl)-2'-deoxycytidine |
| R1—CHO and Z1—SH | $dC^{CH(R1)SZ1}$ | $C_{12}H_{19}N_3O_5S$ | 5-(2-hydroxyethyl)thiomethyl-2'-deoxycytidine |
| R1—CHO and Z2—SH | $dC^{CH(R1)SZ2}$ | $C_{13}H_{20}N_4O_6S$ | 5-(2-amino-2-carboxyethyl)thiomethyl-2'-deoxycytidine |
| R1—CHO and Z3—SH | $dC^{CH(R1)SZ3}$ | $C_{20}H_{26}N_8O_7S$ | 5-(5'-adenosyl)thiomethyl-2'-deoxycytidine |
| R1—CHO and Z4—SH | $dC^{CH(R1)SZ4}$ | $C_{12}H_{20}N_4O_4S$ | 5-(2-aminoethyl)thiomethyl-2'-deoxycytidine |
| R1—CHO and Z5—SH | $dC^{CH(R1)SZ5}$ | $C_{14}H_{22}N_3O_6S_2$ | 5-(2,3-dihydroxy-4-mercaptobutyl)thiomethyl-2'-deoxycytidine |
| R1—CHO and Z2—SeH | $dC^{CH(R1)SeZ2}$ | $C_{13}H_{20}N_4O_6Se$ | 5-(2-amino-2-carboxyethyl)selenomethyl-2'-deoxycytidine |
| R1—CHO and Z4—SeH | $dC^{CH(R1)SeZ4}$ | $C_{12}H_{20}N_4O_4Se$ | 5-(2-aminoethyl)selenomethyl-2'-deoxycytidine |
| R1—CHO and Z6—NH | $dC^{CH(R1)NHZ6}$ | $C_{10}H_{16}N_4O_5$ | 5-hydroxyaminomethyl-2'-deoxycytidine |

New derivatives of 2'-deoxycytidine formed in DNA upon treatment with compound I or sequentially with compounds I and II in the presence of a methyltransferase were obtained in Examples 1-12:

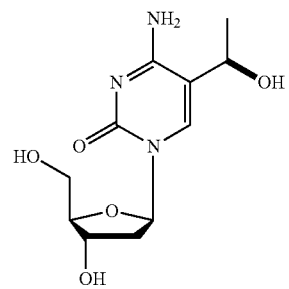

$dC^{CH(OH)R2} = dC^{CH(OH)CH_3}$ 5-(1-hydroxyethyl)-2'-deoxycytidine

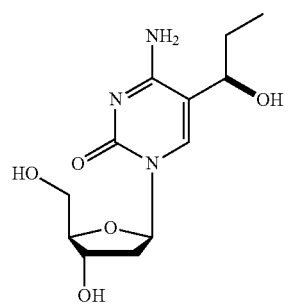

dC^{CH(OH)R3} = dC^{CH(OH)CH_2CH_3}

5-(1-hydroxypropyl)-2'-deoxycytidine

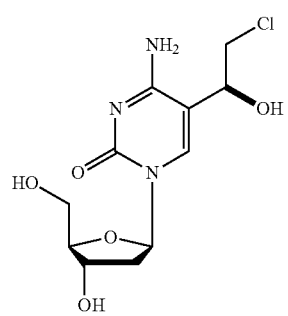

dC^{CH(OH)R4} = dC^{CH(OH)CH_2Cl}

5-(2-chloro)-1-hydroxyethyl)-2'-deoxycytidine

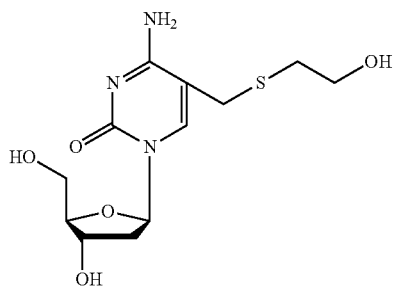

dC^{CH(R1)SZ1} = dC^{CH_2SCH_2CH_2OH}

5-(2-hydroxyethyl)thiomethyl-2'-deoxycytidine

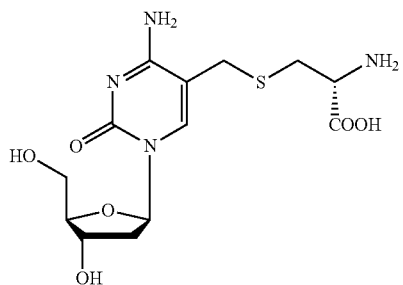

dC^{CH(R1)SZ2} = dC^{CH_2SCH_2CH(COOH)NH_2}

5-(2-amino-2-carboxyethyl)thiomethyl-2'-deoxycytidine

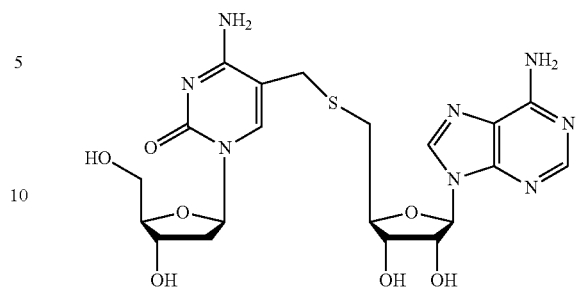

dC^{CH(R1)SZ3} = dC^{CH_2S-Ado}

5'-(5'-adenosyl)thiomethyl-2'-deoxycytidine

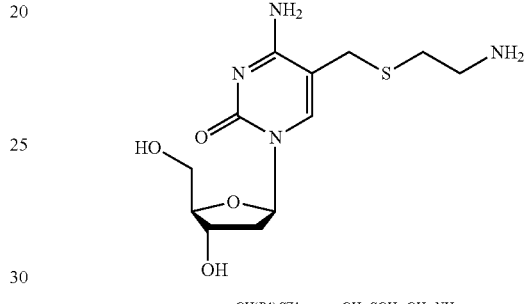

dC^{CH(R1)SZ4} = dC^{CH_2SCH_2CH_2NH_2}

5-(2-aminoyethyl)thiomethyl-2'-deoxycytidine

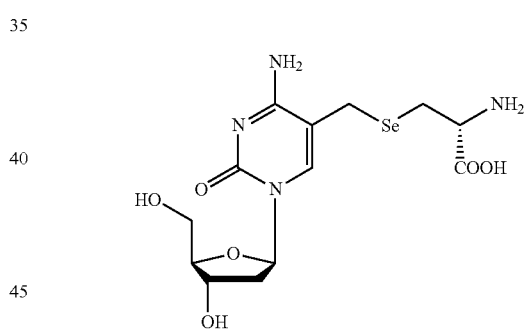

dC^{CH(R1)SeZ2} = dC^{CH_2SeCH_2CH(COOH)NH_2}

5-(2-amino-2-carboxyethyl)selenomethyl-2'-deoxycytidine

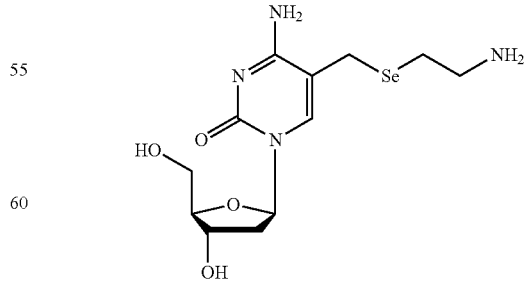

dC^{CH(R1)SeZ4} = dC^{CH_2SeCH_2CH_2NH_2}

5-(2-aminoethyl)selenomethyl-2'-deoxycytidine

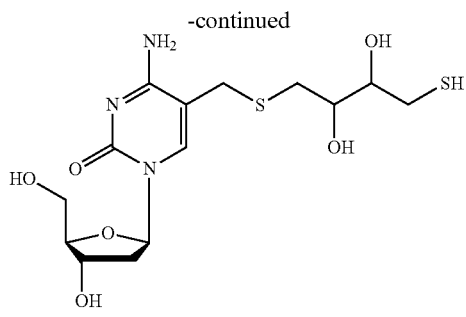

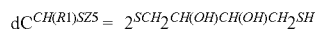

5-(2,3-dihydroxy-4-mercaptobutyl)thiomethyl-2'-deoxycytidine

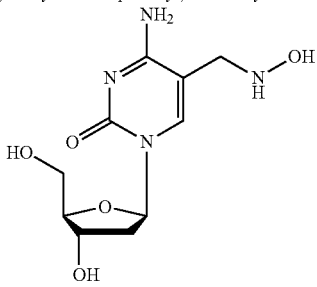

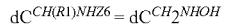

5-hydroxylaminomethyl-2'-deoxycytidine

Examples 13-18

Sequence-specific modifications of internally labeled oligodeoxyribonucleotide duplexes with compound (I) or sequentially with compound (I) and compound (II) in the presence of a DNA cytosine-C5 methyltransferase DNA modification with compounds (I) (R1-CHO=formaldehyde, R2-CHO=acetaldehyde, R3-CHO=propionaldehyde, R4-CHO=2-chloroacetaldehyde, R5-CHO=betaine aldehyde, R6-CHO=benzyloxyacetaldehyde) or sequentially with compound (I) (R1-CHO=formaldehyde) and compound (II) (Z1-SH=2-mercaptoethanol, Z2-SH=L-cysteine, Z3-SH=5'-thio-5'-deoxyadenosine, Z4-SH=cysteamine, Z5-SH=1,4-dithiothreitol, Z2-SeH=L-selenocysteine, Z4-SeH=selenocysteamine, Z6-NH$_2$=hydroxylamine) was investigated in the presence of a directing DNA cytosine-5 MTase M.HhaI, M.SssI, M.HpaII or M.AluI. M.HhaI recognizes the double-stranded DNA sequence 5'-GCGC-3' and naturally transfers the methyl group of S-adenosyl-L-methionine (SAM or AdoMet) to the C5 position of the inner cytosine residue (underlined). Accordingly, other DNA methyltransferases perform a similar reaction but they recognize different DNA target sequences: M.SssI (recognition target CG), M.HpaII (recognition target CCGG) or M.AluI (recognition target AGCT). Analysis of modifications of a target cytosine residue in the presence of a DNA cytosine-C5 methyltransferase was performed using internally labeled duplex oligodeoxyribonucleotides. Internally labeled duplex oligodeoxyribonucleotides contained a cognate target sequence of a DNA methyltransferase in which a target cytosine residue (or a target residue and another cytosine residue for M.HhaI) were 33P-labeled. Following a modification reaction, a duplex oligodeoxynucleotide was enzymatically fragmented to 2'-deoxynucleoside-5'-monophosphates and then analyzed by TLC and autoradiography permitting selective observation of modifications of the target nucleotide.

The duplexes oligodeoxyribonucleotide III:IV (unmethylated duplex for M.HhaI), V:VI (hemimethylated duplex for M.HhaI), VII:VIII (duplex for M.HpaII and M.SssI) and IX:X (duplex for M.AluI) was produced by mixing equal molar amounts (150 µM) of complementary single-stranded oligodeoxyribonucleotide III (SEQ ID NO:3) (5'-TCGGATGT-TGTGGGTCA) and IV (SEQ ID NO:4) (3'-GCCTACAA-CACCCAGTCGCGTACTATCACAT); V (5'-TCGGATGTTGTGGGTCAG) (SEQ ID NO:5) and VI (SEQ ID NO:6) (3'-GCCTACAACACCCAGTCGMGTACTAT-CACAT); VII (SEQ ID NO:7) (5'-TGACCCACGCTCGCC) and VIII (SEQ ID NO:8) (3'-ACTGGGTGCGAGCGGGC-CTCTATTTAATACA); IX (SEQ ID NO:9) (5'-CGCGCCAT-TCCTGCGA) and X (SEQ ID NO:10) (3'-GCGCGGTAAG-GACGCTCGAAATCCTAT) in water, heating at 95° C. for 5 min and slow cooling to room temperature. Labeled duplexes were prepared by mixing DNA duplex (400 nM), dATP, dGTP and dTTP (33 µM of each), [α-33P]CTP (1.5 µM, Hartmann Analytic, Germany) and Klenow Fragment (0.16 u/µL, Fermentas Life Sciences) and incubating in Klenow reaction buffer at 37° C. for 30 min following incubation at 75° C. for 15 min. Samples containing 125 nM M.HhaI, 1000 nM M.HpaII, 5-10 u/µl M.AluI or 0.4-0.8 u/µl M.SssI and 20-100 nM DNA duplexes in buffer (5-20 µL, 50 mM MOPS, 50 mM MES pH 7.0 (for M.HhaI) and pH 7.5 (for other methyltransferases), 1 mM Na2EDTA, 15 mM NaCl, 0.2 mg/ml bovine serum albumin, 5% glycerol) were treated with compound (I) (R=R1-R6, R1-CHO-13 mM, R2-CHO-800 mM, R3-CHO, R4-CHO-200 mM, R5-CHO, R6-CHO-100 mM) and incubated for 1 hour. Sequential coupling of compounds (I) and (II) was performed by first incubating a duplexes oligodeoxyribonucleotide with a DNA methyltransferase and compound (I) (R1-CHO 13 mM), and then adding compound (II) (Z1-SH=2-mercaptoethanol, 300 mM; Z2-SH=L-cysteine, 50 mM; Z3-SH=5'-thio-5'-deoxyadenosine, 400 µM; Z4-SH=cysteamine, 12 mM; Z5-SH=DTT, 50 mM; Z2-SeH=Se-cysteine, 1 mM; Z4-SH=Se-cysteamine, 1.2 mM; Z6-NH=hydroxylamine, 50 mM) and incubated for 1 hour at room temperature. DNA was then precipitated with 3 volume of ethanol, dissolved in nuclease BAL31 buffer (5 µL) with nuclease BAL31 (0.4 u) (Fermentas Life Sciences) and incubated for 2 hours at 30° C. 0.5-3 µl aliquotes were spotted on TLC plates (PEI CelluloseF, 20×20 cm, Merck). TLC plates were eluted with isobutyric acid/water/conc. ammonia, (66:17:4, vol/vol/vol). Plates were dried overnight and radioactive bands were autoradiographed to an imaging plate (Fujifilm, Japan) followed by scanning with a FLA-5100 phosphoimager. Radioactive spots were quantitated using MultiGauge software (Fujifilm). Modified 2'-deoxycytidine-5'-monophosphates (dXMP) were detected as new radioactive spots in addition to the major spot of 2'-deoxycytosine-5'-monophosphate (dCMP). The position of a modified nucleotide (X) relative to that of the unmodified C nucleotide (dCMP) (Rc(X)=R$_f$(dXMP)/R$_f$(dCMP)) was determined and was used for its chromatographic identification.

Example 13

Target nucleotide analysis in a cognate, premethylated and non-specific duplex oligodeoxyribonucleotide after treatment with an aldehyde in the presence of M.HhaI.

Figure 3:
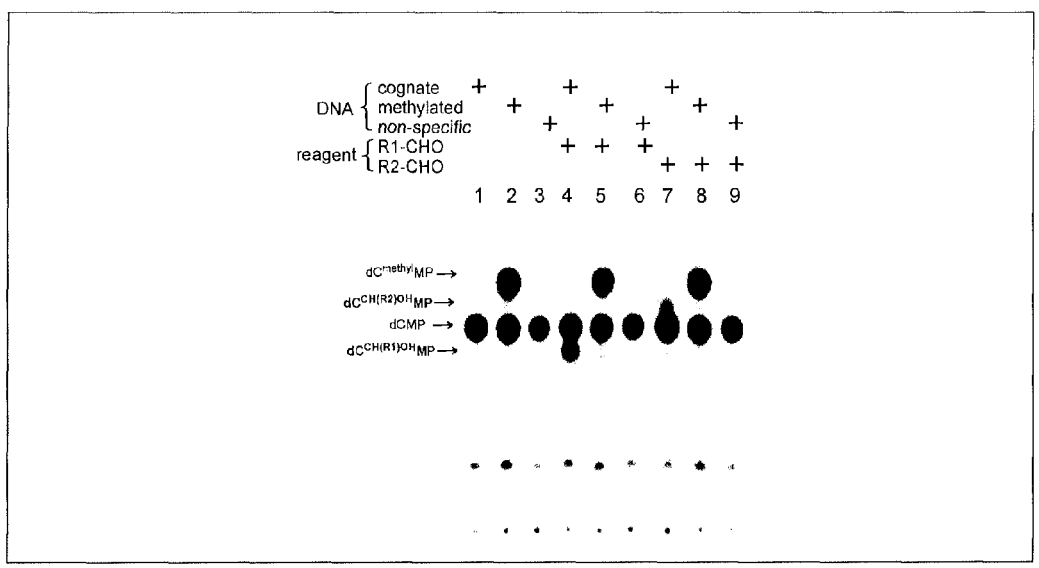
FIG. 3: TLC analysis of [$^{33}$P]-labeled 2'-deoxycytidine-5'-monophosphates of enzymatically fragmented cognate, methylated and non-specific duplex oligodeoxynucleotides, obtained after treatment with M.HhaI. Reactions, containing internally [$^{33}$P]-labeled 20 nM DNA duplexes III:IV (cognate; lanes 1, 4, 7), M.HhaI-premethylated III:IV (methylated, lanes 2, 5, 8) or VII:VIII (non-specific; lanes 3, 6, 9) and 125 nM M.HhaI (lanes 1-9) were treated with 13 mM R1-CHO (lanes 4-6) or 800 mM R2-CHO (lanes 7-9) for 1 hour at room temperature. Gray arrows indicate new products formed upon modification of the target nucleotide. Arrows point corresponding to new modification products. The chemical group —CH(R)OH is attached to the C5 position of dCMP, where R1=—H, R2=—CH$_3$.

Non-specific duplex oligodeoxyribonucleotide (VII:VIII) was used to investigate the specificity of the aldehyde coupling reaction to the target site of methyltransferases and premethylated cognate sequence containing duplex oligodeoxyribonucleotide (premethylated III:IV) to investigate if the reaction is unique for cytosine but not 5-methylcytosine. A new product with Rc of 0.85 was observed in reaction with the cognate DNA duplex is consistent with the formation of 5-hydroxymethylcytosine at the target cytosine residue (lane 4). No new products were observed with the non-specific duplex indicating that the coupling reaction is specific for the cognate target site (FIG. 3, lanes 6, 9). Prior enzymatic methylation of the target cytosine at the GCGC site with M.HhaI and AdoMet leads to the formation of 5-methylcytposine at the target position, which blocks the coupling of compound (I) in the presence of M.HhaI (FIG. 3, compare lanes 4 and 5, 7 and 8). Thus the aldehyde coupling in the presence of M.HhaI can be used for modification of the target cytosine residues in unmethylated, but not M.HhaI-premethylated target sites.

Example 14

Figure 4:
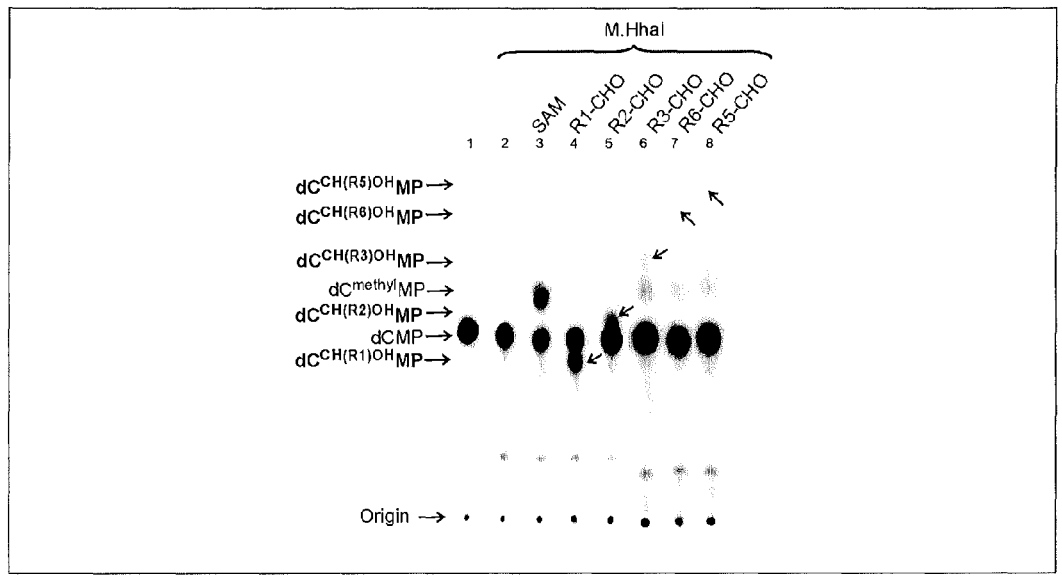
FIG. 4: TLC analysis of [$^{33}$P]-labeled 2'-deoxycytide-5'-monophosphates of enzymatically fragmented duplex oligodeoxynucleotides obtained after treatment with M.HhaI. Reactions, containing 20 nM oligodeoxynucleotide duplex III:IV and 125 nM M.HhaI were treated with 200 µM AdoMet (lane 3), 13 mM R1-CHO (lane 4), 800 mM R2-CHO (lane 5), 200 mM R3-CHO (lane 6), 100 mM R5-CHO (lane 8) or 100 R6-CHO (lane 7) for one hour at room temperature. Control lanes contained no M.HhaI (lane 1) or exogenous reagent (lane 2). Arrows point corresponds to new modification products. The chemical group —CH(R)OH is attached to the C5 position of dCMP, where R1=—H, R2=—CH$_3$, R3=—CH$_2$CH$_3$, R4=—CH$_2$Cl, R5=—CH$_2$N$^+$(CH$_3$)$_3$, R6=—CH$_2$OCH$_2$C$_6$H$_5$.

Target nucleotide analysis in a duplex oligodeoxyribonucleotide after treatment with an aldehyde and the HhaI DNA cytosine-5 methyltransferase (M.HhaI) TLC analysis of modification products obtained after treatment of a DNA-M.HhaI complex with formaldehyde (R1-CHO), acetaldehyde (R2-CHO), propionaldehyde (R3-CHO), betaine aldehyde (R5-CHO) and benzyloxyacetaldehyde (R6-CHO) indicated the formation of new modified nucleotides with measured Rc values of 0.85, 1.1, 1.5, 1.9 and 1.7, respectively (See FIG. 4). No new product is observed in the absence of compound (I) or M.HhaI. Thus coupling of aldehydes R—CHO (R=R1-R6) is directed to the target cytosine residue in the presence of M.HhaI.

Example 15

Figure 5:
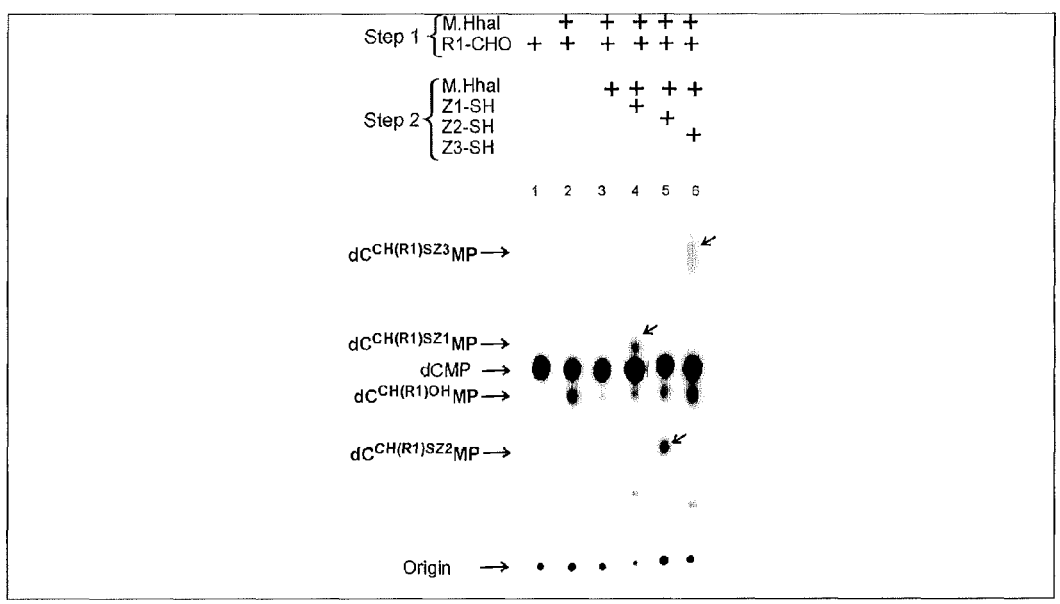
FIG. 5: TLC analysis of [$^{33}$P]-labeled 2'-deoxycytidine-5'-monophosphates of enzymatically fragmented duplex oligodeoxynucleotides obtained after sequential treatment with compound (I) and compound (II) in the presence of M.HhaI. 40 nM oligodeoxyribonucleotide duplex III:IV and 250 nM M.HhaI were incubated with 13 mM R1-CHO for one hour at room temperature (Step 1). R1-CHO modified DNA was treated with 750 nM M.HhaI for 2 hours in the absence (lanes 3 and 4) or presence of 300 mM Z1-SH (lane 4), 50 mM Z2-SH (lane 5) or 400 µM Z3-SH (lane 6) (Step 2). Control lane 1 contained no M.HhaI. Arrows point to spots corresponding to new modification products. The chemical groups —CH(R)OH or —CH(R)SZ are attached to the C5 position of dCMP, where R1=—H, Z1=—CH$_2$CH$_2$OH, Z2=—CH$_2$CH(CO$_2$H)NH$_2$, Z3= —5'-adenosyl.

Target nucleotide analysis in a duplex oligodeoxyribonucleotide after sequential treatment with formaldehyde and compound II in the presence of the HhaI DNA cytosine-5 methyltransferase (M.HhaI) TLC analysis of modification products obtained after treatment of a DNA-M.HhaI complex with formaldehyde (R1-CHO), and then with 2-mercaptoethanol (Z1-SH), L-cysteine (Z2-SH) or 5'-deoxy-5'-thioadenosine (Z3-SH) indicated the formation of new modified nucleotides with measured Rc values of 0.85, 1.1, 1.5, 0.55 and 1.6, respectively (See FIG. 5). No new product is observed in the absence of compound (I), compound (II) or M.HhaI. Thus sequential coupling of formaldehyde (R1-CHO) and compound II (Z=Z1-Z3) is directed to the target cytosine residue in the presence of M.HhaI.

Example 16

Figure 6:
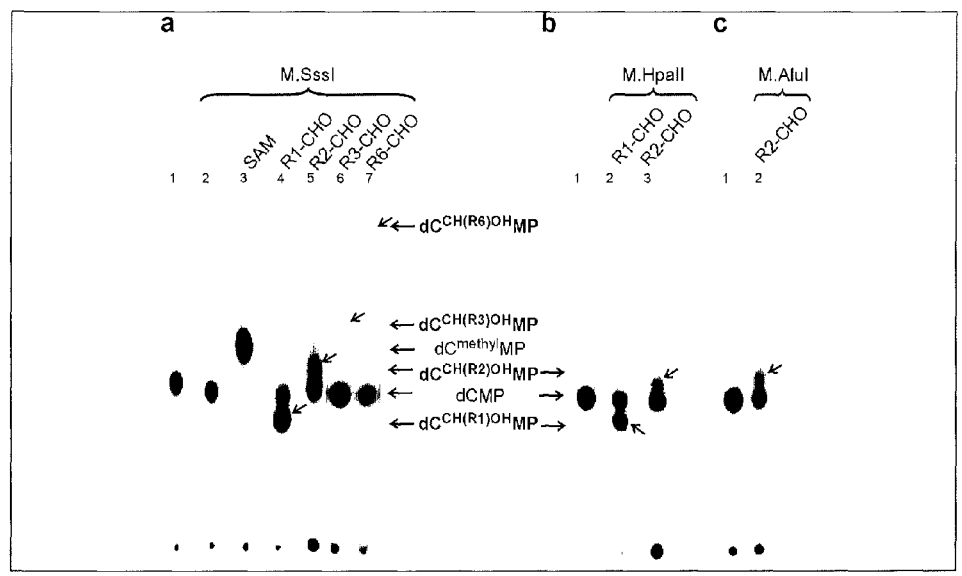
FIG. 6: TLC analysis of [$^{33}$P]-labeled 2'-deoxycytidine-5-monophosphates of enzymatically fragmented duplex oligodeoxynucleotides obtained after treatment with M.SssI, M.HpaII or M.AluI and compound (I). Reactions, containing 20 nM (a), 40 nM (b) or 105 nM (c) oligodeoxynucleotide duplex VII:VIII (a, b) or IX:X (c) and 0.8 u/µl M.SssI (a), 600 nM M.HpaII (b) or 10 u/µl M.AluI (c) were treated with 200 µM AdoMet (a lane 3), 13 mM R1-CHO (a lane 4; b lane 2), 800 mM R2-CHO (a lane 5; b lane 3; lane 2), 200 mM R3-CHO (a lane 6) or 100 mM R6-CHO (a lane 7) for one hour at room temperature. Control lanes contained no MTase (panels a-c, lane 1) or exogenous reagent (panel a, lane 2). Arrows point at spots corresponding to new modification products. The chemical groups —CH(R)OH are attached to the C5 position of dCMP, where R1=—H, R2=—CH₃, R3=—CH₂CH₃, R4=—CH₂Cl and R6=—CH₂OCH₂C₆H₅.

Target nucleotide analysis in a duplex oligodeoxyribonucleotide after treatment with an aldehyde and the SssI DNA cytosine-5 methyltransferase (M.SssI) TLC analysis of modification products obtained after treatment of a DNA-M.SssI complex with formaldehyde (R1-CHO), acetaldehyde (R2-CHO), propionaldehyde (R3-CHO) and benzyloxyacetaldehyde (R6-CHO) indicated the formation of new modified nucleotides with measured Rc values of 0.85, 1.1, 1.5 and 1.7, respectively (see FIG. 6a). These products were chormatogrphically identical with those formed in the presence of M.HhaI. No new product is observed in the absence of compound (I) or M.SssI. Thus coupling of aldehydes R—CHO (R=R1-R3, R6) is directed to the target cytosine residue in the presence of M.SssI.

Example 17

Target nucleotide analysis in a duplex oligodeoxyribonucleotide after treatment with an aldehyde and the HpaII DNA cytosine-5 methyltransferase (M.HpaII) TLC analysis of modification products obtained after treatment of a DNA-M.HpaII complex with formaldehyde (R1-CHO) and acetaldehyde (R2-CHO) indicated the formation of new modified nucleotides with measured Rc values of 0.85 and 1.1, respectively (see FIG. 6b). These products were chormatographically identical with those formed in the presence of M.HhaI. No new product is observed in the absence of compound (I) or M.HpaII. Thus coupling of aldehydes R—CHO (R=R1,R2) is directed to the target cytosine residue in the presence of M.HpaII.

Example 18

Target nucleotide analysis in a duplex oligodeoxyribonucleotide after treatment with an aldehyde and the AluI DNA cytosine-5 methyltransferase (M.AluI) TLC analysis of modification products obtained after treatment of a DNA-M.AluI complex with acetaldehyde (R2-CHO) and propionaldehyde (R3-CHO) indicated the formation of new modified nucleotides with measured Rc values of 1.1 and 1.5, respectively (see FIG. 6c). These products were chormatographically identical with those formed in the presence of M.HhaI. No new product is observed in the absence of compound (I) or M.AluI. Thus coupling of aldehydes R—CHO (R=R2,R3) is directed to the target cytosine residue in the presence of M.AluI Examples 19-21

Sequence-specific modifications of large DNA molecules with compound (I) in the presence of a DNA cytosine-C5 methyltransferase.

Sequence-specific modifications with formaldehyde (R1-CHO) and acetaldehyde (R2-CHO) by DNA cytosine-C5 methyltransferases HhaI, SssI and HpaII were investigated using a DNA protection assay. This assay makes use of the fact that DNA methyltransferase-catalyzed modifications of nucleobases within the recognition sequence of restriction endonucleases can protect the DNA against fragmentation of these enzymes. DNA containing unmodified target sites of a restriction endonuclease is readily fragmented by the restriction endonuclease, whereas covalent modification of the target sites blocks the DNA cleavage. Occurrence of fragmentation is then analyzed by agarose gel electrophoresis.

Example 19

Sequence-specific modification of a 618 bp DNA fragment with formaldehyde or acetaldehyde in the presence of M.HhaI.

A 618 bp fragment of plasmid pUC18 (pUC-618), which contains a single target site for M.HhaI, was used as a DNA substrate. pUC-618 was prepared by PCR amplification of the pUC19 template (Fermentas Life Sciences) using Dir (5'-AACGTTGTTGCCATTGCTAC) (SEQ ID No:11) and Rev (5'-GCTCATGAGACAATAACCCTGA) (SEQ ID No:12) primers and Taq DNA Polymerase (Fermentas Life Sciences). The PCR fragment was purified by Sephacryl S-400 (GE Healthcare) following the precipitation by ethanol. pUC-618 contains a single target site for M.HhaI.

Modification reactions containing 100 nM of pUC-618 and 50 nM M.HhaI were incubated in buffer (50 mM MOPS, 50 mM MES pH 7.0, 1 mM Na2EDTA, 15 mM NaCl, 0.2 mg/ml bovine serum albumin, 5% glycerol) with 13 mM formaldehyde (R1-CHO) or 800 mM acetaldehyde (R2-CHO) for 1 hour at room temperature. Reactions were stopped by heating at 75° C. for 20 min, and treatment with R.Hin6I restriction endonuclease was performed according to manufacturer's recommendations (Fermentas Life Sciences). Samples were supplemented with ⅙ of 6× Loading Dye Solution and analyzed by 2% agarose gel electrophoresis.

Figure 7:
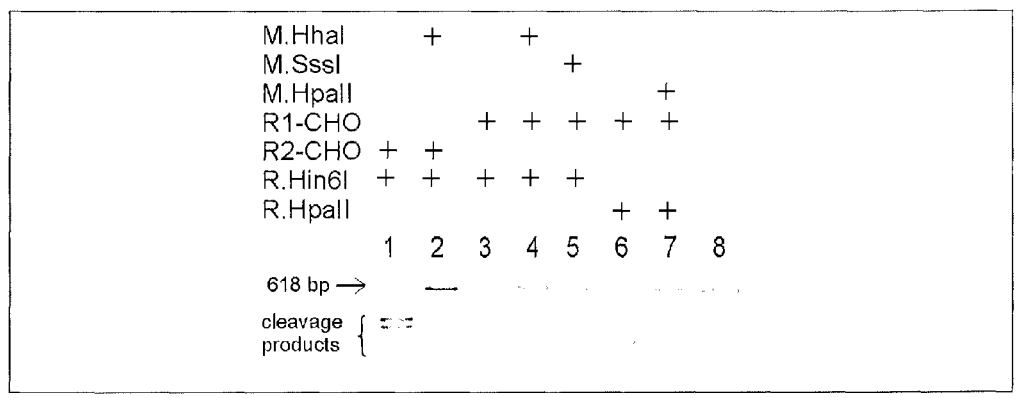
FIG. 7: Restriction endonuclease analysis of methyltransferase-directed modification of 618 bp PGR fragment with compound (I). 100 nM 618 bp PGR fragment (1 M.HhaI recognition site, 32 M.SssI recognition sites, 2 M.HpaII recognition site) and 50 nM M.HhaI (lane 2, 4), 500 nM M.SssI (lane 5) or 1000 M.HpaII (lane 7) were incubated with 13 mM R1-CHO (lanes 3-7) or 800 mM R2-CHO (lanes 1, 2) for 1 hour at room temperature. The modified DNA was then fragmented with a restriction endonuclease R.Hin6I (lanes 1-5) or R.HpaII (lane 6, 7) and analyzed by agarose gel electrophoresis. Control lanes lacked MTase (lanes 1, 3, 6) or both MTase and exogenous reagent (lane 8).

FIG. 7 shows that action of formaldehyde (R1-CHO) (lanes 2, 3) or acetaldehyde (R2-CHO) (lanes 1, 2) in the presence of M.HhaI renders the GCGC site fully or nearly fully resistant to R.Hin6I cleavage, respectively. Thus aldehyde coupling in the presence of M.HhaI leads to efficient modification of a GCGC target site in a DNA fragment.

Example 20

Sequence-specific modification of a 618 bp DNA fragment with formaldehyde in the presence of M.SssI.

The pUC-618 fragment (see above), which contains 32 target sites for M.SssI, was used as a DNA substrate. Modification reactions containing 100 nM of pUC-618 and 500 nM M.SssI were incubated with 13 mM formaldehyde (R1-CHO) for 1 hour at room temperature in buffer (50 mM MOPS, 50 mM MES pH 7.5, 1 mM Na2EDTA, 15 mM NaCl, 0.2 mg/ml bovine serum albumin, 5% glycerol). Reactions were stopped by heating at 75° C. for 20 min, and treatment with R.Hin6I restriction endonuclease was performed according to manufacturer's recommendations (Fermentas Life Sciences). Samples were supplemented with ⅙ of 6× Loading Dye Solution and analyzed by 2% agarose gel electrophoresis.

FIG. 7 shows that action of formaldehyde (R1-CHO) in the presence of M.SssI renders the GCGC site 70% resistant to cleavage with R.Hin6I (lines 3, 5). Thus aldehyde coupling in the presence of M.SssI leads to efficient modification is the GCGC target site in a DNA fragment.

Example 21

Sequence-specific modification of a 618 bp DNA fragment with formaldehyde in the presence of M.HpaII.

The pUC-618 fragment (see above), which contains two target sites for M.HpaII, was used as a DNA substrate. Modification reactions containing 100 nM pUC-618 and 1000 nM M.HpaII were incubated with 13 mM formaldehyde (R1-CHO) for 1 hour at room temperature in buffer (50 mM MOPS, 50 mM MES pH 7.5, 1 mM Na2EDTA, 15 mM NaCl, 0.2 mg/ml bovine serum albumin, 5% glycerol). Reactions were stopped by heating at 75° C. for 20 min, and treatment with R.HpaII restriction endonuclease was performed according to manufacturer's recommendations (Fermentas Life Sciences). Samples were supplemented with ⅙ of 6× Loading Dye Solution and analyzed by 2% agarose gel electrophoresis.

FIG. 7 shows that action of formaldehyde (R1-CHO) in the presence of M.HpaII renders the CCGG sites 70% resistant to cleavage with R.HpaII (lanes 7, 8). Thus aldehyde coupling in the presence of M.HpaII leads to efficient modification of CCGG sites in a DNA fragment.

Example 22

Sequence-specific modification of large natural DNA with formaldehyde in the presence of M.HhaI.

Bacteriophage λ DNA (48502 bp, 215 GCGC target sites) was used as a DNA substrate. Modification reactions containing 0.12 mg/ml λ DNA (817 nM GCGC target sites) and 4 µM M.HhaI were incubated with 13 mM formaldehyde (R1-CHO) or 200 µM AdoMet (control) for 1 hour at room temperature as above The reactions were stopped by heating at 75° C. for 20 min. Then, a restriction endonuclease (R.Hin6I, R.AluI, R.MspI or R.BsuRI) was added and DNA cleavage was performed according to the manufacturer's recommendations (Fermentas Life Sciences). Reactions were stopped by treatment with proteinase K (0.1 mg/ml), SDS (0.5%) at 55° C. for 1 hour. Samples were supplemented with ⅙ of 6× Loading Dye Solution and analyzed by 1% agarose gel electrophoresis.

Figure 8:
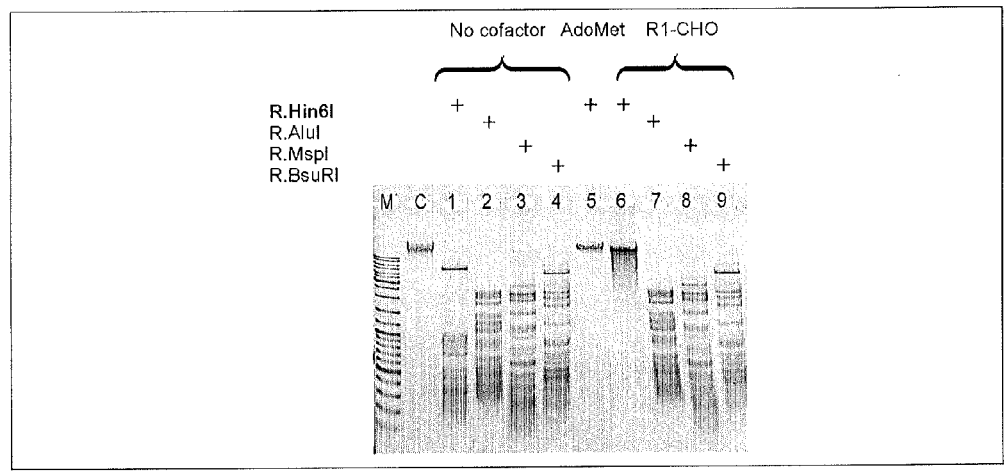
FIG. 8: Restriction endonuclease analysis of methyltransferase-directed modification of bacteriophage λ DNA with compound (I). Modification reactions containing λ DNA (0.82 μM HhaI sites), M.HhaI (4 μM), cofactor (200 μM AdoMet, lane 5) or 13 mM R1-CHO (lanes 6-9) were incubated for 1 hour at room temperature. The modified DNA was then fragmented with a restriction endonuclease R.Hin6I (lanes 1, 5, 6), R.AluI (lanes 2, 7), R.MspI (lanes 3, 8) or R.BsuRI (lanes 4, 9) and analyzed by agarose gel electrophoresis. Lane M, DNA length marker (GeneRuler™ DNA Ladder, Fermentas Life Sciences); lane C, bacteriophage λ DNA control. M.HhaI-directed modification of DNA with HCHO occurs in a sequence-specific manner, since the endonuclease cleavage is blocked at the GCGC sites (lane 6), but not at the AGCT, CCGG or GGCC sites (lanes 7-9).

FIG. 8 shows that action of formaldehyde (R1-CHO) in the presence of M.HhaI renders the GCGC sites in lambda DNA largely resistant to cleavage with a GCGC-specific restriction endonuclease (R.Hin6I), although the modified DNA was readily fragmented by restriction nucleases acting at other target sites, confirming sequence-specific modification of DNA. M.HhaI-directed modification of DNA with formaldehyde (R1-CHO) thus occurs in a sequence-specific manner, since the endonuclease cleavage is blocked at the GCGC sites (lane 6), but not at the AGCT, CCGG or GGCC sites (lanes 7-9).

Example 23

Sequence-specific fluorescent labeling of plasmid DNA using sequential treatment with formaldehyde and L-cysteine in the presence of M.HhaI.

Sequence-specific fluorescent labeling of plasmid pUC19 DNA was achieved by DNA methyltransferase-directed sequential coupling of formaldehyde (R1-CHO) and L-cysteine (Z2-SH) followed by chemo-selective ligation with an amine-reactive fluorescent label (see Scheme 2).

pUC19 DNA (30 µL, 0.21 mg/ml, 2 µM of M.HhaI recognition sites), M.HhaI (8 µM) and formaldehyde (R1-CHO, 13 mM) were incubated for 1 hour at room temperature; freshly diluted L-cysteine (Z2-SH) was added to a 50 mM concentration and incubation continued for 1 hour. The sample was diluted to 200 µL and modified DNA purified by phenol/chloroform extractions (1×200 µL phenol; 2×200 µL 25:24:1 phenol:chloroform:isoamyl alcohol; 3×200 µL chloroform) followed by isopropanol precipitation. DNA was dissolved in 30 µl of 0.15 M sodium hydrogencarbonate, pH 8.8 and treated with 300 µM 6-[Fluorescein-5(6)-carboxamido]hexanoic acid N-hydroxysuccinimide ester (dissolved in dimethylsulfoxide, Fluka) in for 1 hour at room temperature in the dark. DNA was purified with Nucleotide Removal Kit (Qiagen), fragmented with R.FspBI (Fermentas Life Sciences) and analyzed by 2% agarose gel electrophoresis (10 V/cm) in the absence of ethidium bromide. Gels were first scanned with a Fuji FLA-5100 imaging system using a 473 nm laser and then inspected in a UV-imager after staining with ethidium bromide. Control reactions carried out without M.HhaI show no visible DNA fragments in the absence of ethidium bromide staining. The fluorescence intensity distribution in four pUC19-FspBI fragments is fully consistent with the positions and numbers of the HhaI sites in the original plasmid confirming sequence-specific labeling of the plasmid DNA (Table 2).

TABLE 2

| Fluorescence intensity distribution in R.FspBI-pUC19 fragments | | | |
|---|---|---|---|
| Fragment (size, bp) | Number of HhaI sites | Calculated peak area, % | Observed peak area, % |
| F1 (1221) | 7 | 41 | 40 ± 2 |
| F2 (877) | 7 | 41 | 43 ± 3 |
| F3 (335) | 1 | 6 | 6 ± 1 |
| F4 (253) | 2 | 12 | 11 ± 1 |

Figure 9:
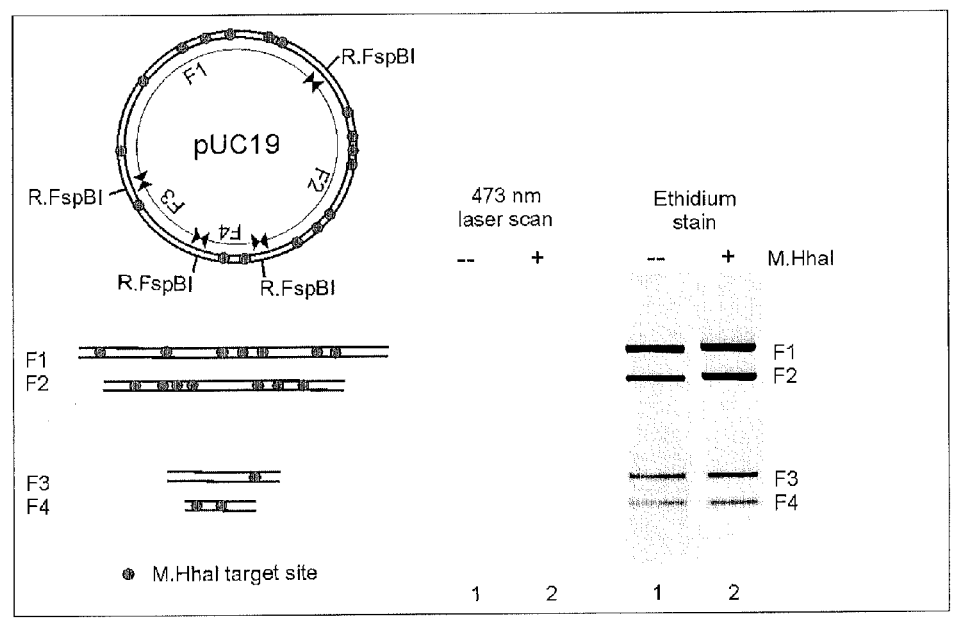
FIG. 9: Sequence-specific covalent labeling of pUC19 plasmid DNA according to the present invention (proof of principle). pUC19 plasmid was sequentially modified with R1-CHO and Z2-SH in the presence of M.HhaI and then treated with a fluorescein N-hydroxysuccinimidyl ester (Fluorescein-NHS). Labeled DNA was fragmented with the R.FspBI endonuclease to produce fragments F1-F4 and analyzed by 2% agarose gel electrophoresis. Imaging of the fluorescein reporter was performed using a 473 nm laser scanner (left panel), DNA fragments were visualized after staining with ethidium bromide (right panel). Lane 1, control with M.HhaI omitted. Lane 2 in the left panel shows that the distribution of fluorescence intensity in the four fragments is consistent with the number (7, 7, 1 and 2, respectively) of HhaI sites (shown in grey balls) indicating sequence-specific labeling of plasmid DNA.

As can be seen from Table 2, the fluorescence intensity distribution in R.FspBI-pUC19 fragments (see FIG. 9) indicates that sequence-specific labeling of plasmid DNA is achieved by sequential treatment with formaldehyde and L-cysteine in the presence of M.HhaI and subsequent modification with a fluorescein-NHS ester.

The invention claimed is:

1. A method of using non-cofactor compounds comprising providing non-cofactor compounds, represented by formulas (I) or (II)

wherein R and Z are independently selected from H, D, $C_1$-$C_{12}$-alkyl, or -LX, wherein X represents a functional group or a reporter group attached via a linker group L, and QH is selected from —SH, —SeH, —NHNH$_2$ or —ONH$_2$, and performing a targeted modification or derivatization of a biomolecule by covalent coupling to the biomolecule in the presence of a directing methyltransferase.

2. A method for targeted modification of a biomolecule comprising incubation the biomolecule with a modifying compound(s) in the presence of a directing methyltransferase under conditions compatible with enzymatic activity of the methytransferase, wherein said targeted modification results from covalent coupling onto the biomolecule of modifying non-cofactor compounds represented by formula (I), or sequentially with compounds (I) and (II)

wherein R and Z are independently selected from H, D, $C_1$-$C_{12}$-alkyl, alkenyl, alkinyl, phenyl or -LX, wherein X represents a functional group or reporter group, attached via a linker group L, and QH is selected from —SH, —SeH, —NHNH$_2$ or —ONH$_2$.

3. The method of claim 1 or claim 2 wherein R is selected from the group consisting of hydrogen, —CH$_3$, —CH$_2$CH$_3$, —CH$_2$Cl, —CH$_2$N$^+$(CH$_3$)$_3$Cl$^-$ and —CH$_2$OCH$_2$C$_6$H$_5$; QH is —SH; and Z is selected from the group consisting of —CH$_2$CH$_2$OH, —CH$_2$CH(CO$_2$H)NH$_2$ and -5'-adenosyl.

4. The method of claim 1 or claim 2 wherein X is independently selected from a primary amino group, a thiol group, a 1,2-diol group, a haloacetamide group, a maleimide group, an aldehyde group, a ketone group, an azido group, an alkyne group, a 1,3-diene function, a dienophilic function, an aryl-halide group, an arylboronic acid group, a terminal haloalkyne group, a terminal silylalkyne group, and a protected amino, thiol, 1,2-diol, hydrazino, hydroxyamino, aldehyde, ketone and 1,2-aminothiol group.

5. The method of claim 1 or claim 2 wherein said biomolecule is a nucleic acid molecule and said methyltransferase is a DNA cytosine-5 methyltransferase.

6. The method of claim 1 or claim 2 for targeted derivatization of a biomolecule, and further comprises any of the following steps:

a) covalent ligation with a compound carrying a chemical reactive group that can be covalently ligated with a functional group X in the modified biomolecule, or b) secondary chemical modification of the biomolecule at the modified target base, wherein secondary modification involves reactions of other attached groups besides the functional group X; or c) secondary internal modification of the biomolecule comprising a further chemical reaction of the attached functional group X with the target base or nearby moieties; or d) enzymatic secondary modification of the 5-hydroxymethylcytosine residue in the modified biomolecule.

7. The method of claim 6, wherein step b) of the secondary chemical modification of the biomolecule at the modified target base comprises a treatment with a mild oxidation reagent followed by further selective chemoligation of the formed carbonyl group with compounds carrying a carbonyl-reactive group, selected from the group consisting of primary amines, hydrazine, hydroxylamine and 1,2-aminothiol.

8. The method of claim 6, wherein step c) of the secondary internal modification of the biomolecule comprises a further chemical reaction of the attached functional group X with the target base or nearby moieties leading to changes of the base-pairing properties of the target base, excision of the target base, strand cleavage or interstrand cross-link in the modified biomolecule.

9. The method of claim 6, wherein step d) of enzymatic secondary modification of the 5-hydroxymethylcytosine residue in the modified biomolecule is performed by at least one of the following:

i) treatment with a UDP-glucose:DNA D-glucosyltransferase and UDP-glucose or derivatives thereof leading to targeted incorporation of D-glucose or a derivative thereof into the biomolecule; or ii) treatment with a 5-hydroxymethylcytosine-DNA deaminase so as to convert 5-hydroxymethylcytosine into 5-hydroxymethyluridine, which conversion is detectable by DNA sequencing; or iii) treatment with a 5-hydroxymethylcytosine-DNA glycosylase, producing an abasic site in the modified DNA strand.

10. The method of claim 1 or claim 2 which is for targeted labeling of a biomolecule comprising modification of the biomolecule to incorporate a reporter group that is suitable as a label and that allows for the identification of the labeled molecule among other unlabeled molecules.

11. The method of claim 10, wherein the label is selected from the group consisting of fluorophores, fluorescence quenchers, chromophores, affinity tags, stable paramagnetic groups, groups containing radioactive or stable rare isotopes, groups containing heavy atoms suitable for phasing X-ray diffraction data, crosslinking agents, nucleic acids cleaving groups, haptens, nanoparticles, beads, and combinations thereof.

12. A method for detecting unmethylated target sites in a biomolecule modified by the method of claim 2, comprising modification of the biomolecule in the presence of a methyltransferase and detecting whether the target sites of said methyltransferase have been modified, wherein modification of the target site of said methyltransferase is indicative of the presence of unmethylated target site.

13. The method of claim 12, wherein the coupled compound interferes with nucleic acid amplification at the recognition sites of the methyltransferase; and unmethylated target sites are detected by testing whether amplification of the nucleic acid molecule at the recognition sites of the methyltransferase has been retarded.

14. The method of claim 12, wherein the coupled compound(s) contains a fluorescent label; and unmethylated target sites are detected by measuring the presence or amount of fluorescence in said nucleic acid molecule.

15. The method of claim 12, wherein the modifying compound(s) is added to a cytosine residue in DNA and cannot be added to a 5-methylcytosine residue.

16. The method of claim 12, wherein a label in a biomolecule is identified by DNA sequencing, hybridization, MALDI-TOF or analysis of nucleoside composition by enzymatic fragmentation and chromatography.

17. A kit for performing the method of claim 2 comprising a directing methyltransferase and non-cofactor compounds (I) or compounds (I) and (II),

wherein R and Z are independently selected from H, D, $C_1$-$C_{12}$-alkyl or -LX, wherein X represents a functional group or reporter group, attached via a linker group L, and QH is selected from —SH, —SeH, —NHNH$_2$ or —ONH$_2$, in separate containers and instructions for performing the method using the kit.

18. The method of claim 1 wherein R and Z are $C_1$-$C_4$-alkyl,or -LX.

19. The method of claim 2 wherein R and Z are $C_1$-$C_4$-alkyl.

20. The method of claim 5 wherein said biomolecule is DNA and said DNA cytosine-5methyltransferase is selected from the group consisting of M.HhaI, M.SssI, M.HpaII and M.AluI or a derivative thereof.

21. The method of claim 7 wherein the mild oxidation reagent is $MnO_2$ or periodic acid.

22. The method of claim 9 wherein the abasic site in the modified DNA strand is further processed.

* * * * *